US011026898B2

(12) United States Patent
Lederman et al.

(10) Patent No.: US 11,026,898 B2
(45) Date of Patent: *Jun. 8, 2021

(54) EUTECTIC FORMULATIONS OF CYCLOBENZAPRINE HYDROCHLORIDE

(71) Applicant: TONIX PHARMA HOLDINGS LIMITED, Dublin (IE)

(72) Inventors: Seth Lederman, South Dartmouth, MA (US); Marino Nebuloni, Rho (IT)

(73) Assignee: Tonix Pharma Holdings Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/518,338

(22) Filed: Jul. 22, 2019

(65) Prior Publication Data

US 2019/0336458 A1 Nov. 7, 2019

Related U.S. Application Data

(63) Continuation of application No. 15/511,287, filed as application No. PCT/US2015/051068 on Sep. 18, 2015, now Pat. No. 10,357,465.

(60) Provisional application No. 62/052,238, filed on Sep. 18, 2014.

(51) Int. Cl.
| | | |
|---|---|---|
| *A61K 31/135* | (2006.01) |
| *A61K 9/16* | (2006.01) |
| *A61K 9/20* | (2006.01) |
| *A61P 25/24* | (2006.01) |
| *A61P 25/22* | (2006.01) |
| *A61P 25/20* | (2006.01) |
| *A61P 25/08* | (2006.01) |
| *A61P 25/04* | (2006.01) |
| *A61P 25/00* | (2006.01) |
| *A61P 21/02* | (2006.01) |
| *A61P 21/00* | (2006.01) |

(52) U.S. Cl.
CPC .......... *A61K 31/135* (2013.01); *A61K 9/1623* (2013.01); *A61K 9/2018* (2013.01); *A61P 21/00* (2018.01); *A61P 21/02* (2018.01); *A61P 25/00* (2018.01); *A61P 25/04* (2018.01); *A61P 25/08* (2018.01); *A61P 25/20* (2018.01); *A61P 25/22* (2018.01); *A61P 25/24* (2018.01)

(58) Field of Classification Search
CPC .. A61K 31/135; A61K 9/1623; A61K 9/2018; A61P 21/00; A61P 21/02; A61P 25/00; A61P 25/04; A61P 25/08; A61P 25/20; A61P 25/22; A61P 25/24
See application file for complete search history.

(56) References Cited

U.S. PATENT DOCUMENTS

| | | |
|---|---|---|
| 4,968,507 A | 11/1990 | Zentner |
| 5,073,543 A | 12/1991 | Marshall |
| 5,120,548 A | 6/1992 | McClelland |
| 5,439,686 A | 8/1995 | Desai |
| 5,498,421 A | 3/1996 | Grinstaff |
| 5,591,731 A | 1/1997 | Kennedy |
| 5,591,767 A | 1/1997 | Mohr |
| 5,639,476 A | 6/1997 | Oshlack |
| 5,674,533 A | 10/1997 | Santus |
| 5,733,566 A | 3/1998 | Lewis |
| 6,096,331 A | 8/2000 | Desai |
| 6,248,363 B1 | 6/2001 | Patel |
| 6,267,985 B1 | 7/2001 | Chen |
| 6,309,663 B1 | 10/2001 | Patel |
| 6,358,944 B1 | 3/2002 | Lederman |
| 6,383,471 B1 | 5/2002 | Chen |
| 6,395,788 B1 | 5/2002 | Iglehart |
| 6,506,405 B1 | 1/2003 | Desai |
| 6,537,579 B1 | 3/2003 | Desai |
| 6,541,523 B2 | 4/2003 | Iglehart |
| 6,720,001 B2 | 4/2004 | Chen |
| 6,749,868 B1 | 6/2004 | Desai |
| 6,753,006 B1 | 6/2004 | Desai |
| 6,761,903 B2 | 7/2004 | Chen |
| 7,105,486 B2 | 9/2006 | Mickle |
| 7,223,735 B2 | 5/2007 | Mickle |
| 7,532,935 B2 | 5/2009 | Maschino |
| 7,655,630 B2 | 2/2010 | Mickle |
| 7,658,945 B2 | 2/2010 | Singh |
| 7,659,253 B2 | 2/2010 | Mickle |
| 7,659,254 B2 | 2/2010 | Mickle |
| 7,662,787 B2 | 2/2010 | Mickle |
| 7,662,788 B2 | 2/2010 | Mickle |
| 7,671,030 B2 | 3/2010 | Mickle |

(Continued)

FOREIGN PATENT DOCUMENTS

| | | |
|---|---|---|
| EP | 2233134 | 9/2010 |
| WO | WO1999018937 | 4/1999 |

(Continued)

OTHER PUBLICATIONS

Faure et al., "Process control and scale-up of pharmaceutical wet granulation processes: a review", 2001, European Journal of Pharmaceutics and Biopharmaceutics, 52(3), pp. 269-277. (Year: 2001).*

Bouffard et al., "Influence of Process Variable and Physicochemical Properties on the Granulation Mechanism of Mannitol in a Fluid Bed", 2005, Drug Development and Industrial Pharmacy, 31(9), pp. 923-933. (Year: 2005).*

Cornel et al., "Precipitation and Transformation of the Three Polymorphs of D-Mannitol", 2010, Ind. Eng. Chem. Res., vol. 49, No. 12, pp. 5854-5862. (Year: 2010).*

(Continued)

*Primary Examiner* — My-Chau T. Tran
(74) *Attorney, Agent, or Firm* — Haley Guiliano LLP; James F. Haley, Jr.

(57) ABSTRACT

The present invention relates to pharmaceutical compositions and methods of manufacturing the same, comprising a eutectic of Cyclobenzaprine HCl and mannitol.

23 Claims, 11 Drawing Sheets

(56) References Cited

U.S. PATENT DOCUMENTS

| | | | |
|---|---|---|---|
| 7,671,031 | B2 | 3/2010 | Mickle |
| 7,674,774 | B2 | 3/2010 | Mickle |
| 7,678,770 | B2 | 3/2010 | Mickle |
| 7,678,771 | B2 | 3/2010 | Mickle |
| 7,682,628 | B2 | 3/2010 | Singh |
| 7,687,466 | B2 | 3/2010 | Mickle |
| 7,687,467 | B2 | 3/2010 | Mickle |
| 7,700,561 | B2 | 4/2010 | Mickle |
| 7,713,936 | B2 | 5/2010 | Mickle |
| 7,718,619 | B2 | 5/2010 | Mickle |
| 7,723,305 | B2 | 5/2010 | Mickle |
| RE41,884 | E | 10/2010 | Garavilla |
| 7,820,788 | B2 | 10/2010 | Desai |
| 7,923,536 | B2 | 4/2011 | Desai |
| 8,093,300 | B2 | 1/2012 | Lederman |
| 8,137,734 | B2 | 3/2012 | Venkatesh |
| 8,138,229 | B2 | 3/2012 | Desai |
| 9,474,728 | B2 | 10/2016 | Lederman |
| 9,636,408 | B2 | 5/2017 | Nebuloni |
| 9,918,948 | B2 | 3/2018 | Lederman |
| 10,117,936 | B2 | 11/2018 | Nebuloni |
| 10,322,094 | B2 | 6/2019 | Nebuloni |
| 10,357,465 | B2 * | 7/2019 | Lederman ............ A61K 31/135 |
| 2003/0077227 | A1 | 4/2003 | Dugger |
| 2003/0077297 | A1 | 4/2003 | Chen |
| 2005/0096327 | A1 | 5/2005 | Caprathe |
| 2005/0181041 | A1 | 8/2005 | Goldman |
| 2006/0073189 | A1 | 4/2006 | Pinney |
| 2007/0141144 | A1 | 6/2007 | Roberts |
| 2007/0196364 | A1 | 8/2007 | Krishnamurthy |
| 2008/0146672 | A1 | 6/2008 | Denton |
| 2009/0054403 | A1 | 2/2009 | Woiwode |
| 2009/0098200 | A1 | 4/2009 | Krayz |
| 2009/0275541 | A1 | 11/2009 | Sullivan |
| 2010/0021507 | A1 | 1/2010 | Bunick |
| 2010/0098832 | A1 | 4/2010 | Venkatesh |
| 2010/0247586 | A1 | 9/2010 | Hugerth |
| 2010/0247649 | A1 | 9/2010 | Palaparthi |
| 2010/0266682 | A1 | 10/2010 | Davar |
| 2011/0062614 | A1 | 3/2011 | Suenaga |
| 2011/0068511 | A1 | 3/2011 | Sowden |
| 2011/0124656 | A1 | 5/2011 | Lederman |
| 2011/0319389 | A1 | 12/2011 | Lederman |
| 2012/0101154 | A1 | 4/2012 | Lederman |
| 2012/0232159 | A1 | 9/2012 | Lederman |
| 2013/0165511 | A1 | 6/2013 | Lederman |
| 2014/0171515 | A1 | 6/2014 | Lederman |
| 2014/0336264 | A1 | 11/2014 | Nebuloni |
| 2015/0065581 | A1 | 3/2015 | Lederman |
| 2016/0030576 | A1 | 2/2016 | Nebuloni |
| 2017/0239195 | A1 | 8/2017 | Nebuloni |
| 2017/0281568 | A1 | 10/2017 | Lederman |
| 2018/0344668 | A1 | 12/2018 | Nebuloni |
| 2019/0022030 | A1 | 1/2019 | Nebuloni |
| 2019/0022031 | A1 | 1/2019 | Nebuloni |
| 2019/0282517 | A1 | 9/2019 | Nebuloni |
| 2019/0358177 | A1 | 11/2019 | Lederman |

FOREIGN PATENT DOCUMENTS

| | | |
|---|---|---|
| WO | WO1999058115 | 11/1999 |
| WO | WO2001012174 | 2/2001 |
| WO | WO2001012175 | 2/2001 |
| WO | WO2001089476 | 11/2001 |
| WO | WO2004035021 | 4/2004 |
| WO | WO2004039320 | 5/2004 |
| WO | WO2005051297 | 6/2005 |
| WO | WO2007038620 | 4/2007 |
| WO | WO2009002770 | 12/2008 |
| WO | WO2009089494 | 7/2009 |
| WO | WO2011062614 | 5/2011 |
| WO | WO2014145156 | 9/2014 |

OTHER PUBLICATIONS

Al-khattawi et al., "Compressed orally disintegrating tablets: excipients evolution and formulation strategies", 2013, Expert Opinion on Drug Delivery, 10(5), pp. 651-663. (Year: 2013).*

Aaronson et al., "Defining and measuring fatigue," Image J. Nurs. Sch., 31:45-50 (1999).

Abd el-Fattah et al., "Enhancement of dissolution rate of hydrochlorothiazide via solid dispersion," Pharmazie, 41:790-793 (1986).

Abernethly et al., "Absolute bioavailability of imipramine: influence of food," Psychoharmacology (Berl.), 83:104-106 (1984).

Amin et al., "Indion 414 as superdisintegrant in formulation of mouth dissolve tablets," Indian Journal of Pharmaceutical Sciences, 68: 117-119 (2006).

Amitai et al., "Distribution of amitriptyline and nortriptyline in blood: role of alpha-1-glycoprotein," Ther. Drug Monit., 15:267-273 (1993).

Amital et al., "Posttraumatic stress disorder, tenderness, and fibromyalgia syndrome: are they different entities?," Journal of Psychosomatic Research, 61(5):663-669 (2006).

Arnold et al., "Antidepressant treatment of fibromyalgia. A meta-analysis and review," Psychosomatics, 41:104-113 (2000).

Bagul, "Current status of table disintegrants: a review," retrieved from [http://www.pharmainfo.net/reviews/current-status-tablet-disintegrantsa-review] (2006) 13 pages.

Balant et al., "Prodrugs for the improvement of drug absorption via different routes of administration," European Journal of Drug Metabolism and Pharmacokinetics,15(2):143-153 (1990).

Balasubramaniam et al., "Effects of superdisintegrants on dissolution of cationic drugs," Dissolution Technologies, 18-25 (2008).

Barker et al., "Identification of a single amino acid, phenylalanine 586, that is responsible for high affinity interactions of tricyclic antidepressants with the human serotonin transporter," Mol. Pharmacol., 50:957-965 (1996).

Barnes et al., "Brainstem noradrenergic system depression by cyclobenzaprine," Neuropharmacology, 19:221-224 (1980).

Bartoli et al., "An atypical case of reverse Takotsubo cardiomyopathy during general anesthesia in a 30-year-old male with post-traumatic stress disorder," J. Cardiothorac Vasc. Anesth., 25:1116-1118 (2011).

Baumann et al., "Amitriptyline pharmacokinetics and clinical response: I. Free and total plasma amitriptyline and nortriptyline," Int. Clin. Psychopharmacol., 1:89-101 (1986).

Bennett et al., "A comparison of cyclobenzaprine and placebo in the management of fibrositis: A double-blind controlled study," Arthritis Rheum., 31:1535-1542 (1988).

Berezhkovskiy et al., "Prediction of the possibility of the second peak of drug plasma concentration time curve after iv bolus administration from the standpoint of the traditional multi-compartmental linear pharmacokinetics," J. Pharm. Sci., 97:2385-2393 (2008).

Bhatt et al., "Development and validation of amitriptyline and its metabolite in human plasma by ultra performance liquid chromatography—tandem mass spectrometry and its application to a bioequivalence study," Biomedical Chromatography, 24:1247-1254 (2010).

Bhowmik et al., "Fast dissolving tablet: an overview," Journal of Chemical and Pharmaceutical Research, 1:163-177 (2009).

Bi et al., "Mechanism of eutectic formation upon compaction and its effects on tablet properties," Thermochimica Acta, 404:213-226 (2003).

Bickel et al., "Buccal absorption and other properties of pharmacokinetic importance of imipramine and its metabolites," J. Pharm Pharmacol., 21:160-168 (1969).

*Bingshen, et al., "Pharmacy of Chinese Materia Medica," Chinese Medicine Science and Technology Publishing House, 384-387 (Feb. 28, 2018) (English Translation).

Blake et al., "The development of a clinician-administered PTSD scale," Journal of Traumatic Stress, 8:75-90 (1995).

Braithwaite et al., "Plasma concentration of amitriptyline and clinical response," Lancet., 17:1297-1300 (1972).

(56) References Cited

OTHER PUBLICATIONS

Breyer-Pfaff et al., "Comparative N-glucuronidation kinetics of ketotifen and amitriptyline by expressed human UDP-glucuronosyltransferases and liver microsomes," Drug Metab. Dispos., 28:869-872 (2000).

Brittain, "A summary of the scholarly activities associated with Center for Pharmaceutical Physics," Journal of Pharmaceutical Physics, vol. 11 (2009) 24 pages.

Brittain, "Profiles of Drug Substances, Excipients, and Related Methodology," Journal of Pharmaceutical Physics, vol. 12 (2010) 14 pages.

Bundgaard, "Novel chemical approaches in prodrug design," Drugs of the Future, 16:443-458.

Cai et al., "A humanized UGT1 mouse model expressing the UGT1A1*28 allele for assessing drug clearance by UGT1A1-dependent glucuronidation," Drug Metab. Dispos., 38:879-886 (2010).

Caillé et al., "Pharmacokinetics of two lorazepam formulations, oral and sublingual, after multiple doses," Biopharmaceutics and Drug Disposition, 4(1):31-42 (1983).

Campbell-Roberts et al., "Quantitative analysis of mannitol polymorphs. X-ray powder diffractometry—exploring preferred orientation effects," J. Pharm. Biomed. Anal., 28:1149-1159 (2002).

Cantini et al., "[Fluoxetin combined with cyclobenzaprine in the treatment of fibromyalgia]," Minerva Med., 85:97-100 (1994) (Abstract in English).

Cavaljuga et al., "Therapeutic effects of two antidepressant agents in the treatment of posttraumatic stress disorder (PTSD)," Bosnian Journal of Basic Medical Sciences, 3(2):12-16 (2003).

Cherukuvada, et al., "Eutectics as improved pharmaceutical materials: design, properties and characterization," Chemical Communications, 50:906-923 (2014).

Commissiong et al., "Cyclobenzaprine: a possible mechanism of action for its muscle relaxant effect," Canadian Journal of Physiology and Pharmacology, 59(1):37-44 (1981).

Cotton et al., "Cyclobenzaprine hydrochloride," Anal Profiles Drug Subs, 17:41-72 (1988).

Cyclobenzaprine (Flexeril), eMedExpert.com—Facts, Oct. 5, 2008 (Oct. 5, 2008), pp. 1-2,URL:http://www.emedexpert.com/facts/cyclobenzaprine-facts.shtml.

Davies et al., "Multiple peaking phenomena in pharmacokinetic disposition," Clinical Pharmacokinetics, 49:351-377 (2010).

Descamps et al., "Transformation of pharmaceutical compounds upon milling and comilling. The role of T(g)," J. Pharm. Sci., 96:1398-1407 (2007).

Dobrinska, "Enterohepatic circulation of drugs," J. Clin. Pharmacol., 29:577-580 (1989).

El-Banna et al., "Physicochemical study of drug binary systems. Part 3: Tolbutamide-urea and tolbutamide-mannitol systems," Pharmazie, 30:788-792 (1975).

El-Banna et al., "The application of solid dispersion technique in the preparation of therapeutic tablets. Part 1: Paracetamol, amylobarbitone, and caffeine tablets," Pharmazie,. 32:511-515 (1977).

Ereshefsky et al., "Pharmacokinetic factors affecting antidepressant drug clearance and clinical effect: evaluation of doxepin and imipramine—new data and review," Clin. Chem., 34:863-880 (1988).

FDA guidance for industry, bioavailability and bioequivalence studies for orally administered drug products—general considerations, US Dept. of Health and Human Services, FDA, Center for Drug Evaluation and Research (2003) 26 pages.

Fleisher, et al., "Clinical predictors of progression to Alzheimer disease in amnestic mild cognitive impairment," Neurology, 68(19):1588-1595 (2007).

Fossaluzza et al., "Combined therapy with cyclobenzaprine and ibuprofen in primary fibromyalgia syndrome," International Journal of Pharmacology Research, 12:99-102 (1992).

Fronczek et al., "Three polymorphs (alpha, beta, and delta) of D-mannitol at 100 K," Acta Crystallographica Section C, 59:o567-o570 (2003).

Fujiwara et al., "Developmental hyperbilirubinemia and CNS toxicity in mice humanized with the UDP glucuronosyltransferase 1 (UGT1) locus," Proc. Natl. Acad. Sci., USA, 107:5024-5029 (2010).

Gai et al., "Bioavailability of a controlled-release cyclobenzaprine tablet and influence of a high fat meal on bioavailability," International Journal of Clinical Pharmacology and Therapeutics, 47(4):269-274 (2009).

Godfrey, "A guide to the understanding and use of tricyclic antidepressants in the overall management of fibromyalgia and other chronic pain syndromes," Archives of Internal Medicine, 156:1047-1052 (1996).

Green et al., "Glucuronidation of amine substrates by purified and expressed UDP-glucuronosyltransferase proteins," Drug Metab. Dispos., 26:860-867 (1998).

Grof et al., "Preliminary comparative trial of proheptatriene and imipramine in the treatment of depressions (an intensive and controlled study)," Activitas Nervosa Superior, 7:288-289 (1965).

Guo et al., "Liquid chromatography-tandem mass spectrometry method for measurement of nicotine N-glucuronide: a marker for human UGT2B10 inhibition," J. Pharm. Biomed. Anal., 55:964-971 (2011).

Hawes, "N+-glucuronidation, a common pathway in human metabolism of drugs with a tertiary amine group," Drug Metab. Dispos., 26:830-837 (1998).

Hiller et al., "Retigabine N-glucuronidation and its potential role in enterohepatic circulation," Drug Metab. Dispos., 27:605-612 (1999).

Honda et al., "Tricyclic analogs cyclobenzaprine, amitriptyline and cyproheptadine inhibit the spinal reflex transmission through 5-HT(2) receptors," European Journal of Pharmacology, 458(1-2):91-99 (2003).

Hucker et al., "Metabolism of cyclobenzaprine in the dog," Drug Metabolism & Disposition, 6(2):184-192 (1978).

Hucker et al., Physiological disposition and metabolism of cyclobenzaprine in the rat, dog, rhesus monkey, and man Drug Metabolism & Disposition, 6:659-672 (1978).

Hucker et al., "Plasma levels and bioavailability of cyclobenzaprine in human subjects," Journal of Clinical Pharmacology, 17:719-727 (1977).

Jorgensen et al., "Pharmacokinetics of amitriptyline infused intravenously in man," European Journal of Clinical Pharmacology, 10:337-341 (1976).

Kaivosaari et al., "N-glucuronidation of drugs and other xenobiotics by human and animal UDP-glucuronosyltransferases," Xenobiotica., 41:652-669 (2011).

Katz et al., "Cyclobenzaprine in the treatment of acute muscle spasm: review of a decade of clinical experience," Clinical Therapeutics, 10(2):216-228 (1988).

Kobayashi et al., "Cyclobenzaprine, a centrally acting muscle relaxant, acts on descending serotonergic systems," European Journal of Clinical Pharmacology, 311:29-35 (1996).

Kornhuber et al., "Identification of new functional inhibitors of acid sphingomyelinase using a structure-property-activity relation model," J. Med. Chem., 51:219-237 (2008).

Krishnan et al., "The molecular neurobiology of depression," Nature, 455:894-902 (2008).

Kubo et al., "Improvement of dissolution rate and oral bioavailability of a sparingly water-soluble drug, (+/−)-5-[[2-(2-naphthalenylmethyl)-5-benzoxazolyl]-methyl]-2,4-thiazolidinedione, in co-ground mixture with D-mannitol," Biol. Pharm. Bull., 20:460-463 (1997).

Lee et al., "Transinactivation of the epidermal growth factor receptor tyrosine kinase and focal adhesion kinase phosphorylation by dietary flavonoids: effect on invasive potential of human carcinoma cells," Biochem. Pharmacol., 67:2103-0114 (2004).

Link et al., "Cardiovascular regulation in mice lacking alpha2-adrenergic receptor subtypes b and c," Science, 273:803-805 (1996).

Miles et al., "An investigation of human and rat liver microsomal mycophenolic acid glucuronidation: evidence for a principal role of UGT1A enzymes and species differences in UGT1A specificity," Drug Metab. Dispos., 33:1513-1520 (2005).

Moldofsky et al., "Effects of bedtime very low dose cyclobenzaprine on symptoms and sleep physiology in patients with fibromyalgia

(56) References Cited

OTHER PUBLICATIONS syndrome: a double-blind randomized placebo-controlled study," Journal of Rheumatology, 38(12):2653-2663 (2011).
Narang et al., "Sublingual mucosa as a route for systemic drug delivery," International Journal of Pharma Sciences, 3:18-22 (2011).
Nelson, "Experimental Determination of 2-component Phase Diagrams," retrieved from http://www.tulane.edu/-sanelson/eens211/2compphasdiag.html, Feb. 7, 2011 (12 pages).
Ohrem et al., "Why is mannitol becoming more and more popular as a pharmaceutical excipient in solid dosage forms?," Pharmaceutical Development and Technology, 19(3):257-262 (2014).
Ohshima et al., "Tissue distribution and metabolism of amitriptyline after repeated administration in rats," Metabolism and Disposition, 22:21-25 (1994).
Overo et al., "Kinetics of nortriptyline in man according to a two compartment model," European Journal of Clinical Pharmacology, 8:343-347 (1975)
PEARLITOL® Product Information (website:www.roquette.conn/-/nnedia/sannple-sharepoint-libraries/nnarconnonline---pharnna/roquette-pharnna-oral-dosage-brochure-pearlitol-nnannitol.pdf) (2012) (22 pages).
Price et al., "Single-dose pharmacokinetics of sublingual versus oral administration of micronized 17 beta-estradiol," Obstetrics and Gynecology, 89(3):340-345 (1997).
Protocol Registration Receipt Jun. 26, 2012, "Comparative bioavailability of sublingual TNX-102, oral and intravenous cyclobenzaprine in healthy adults" 4 pages.
Razaghi et al., "Investigation of cyclobenzaprine hydrochloride release from oral osmotic delivery systems containing a water-swellable polymer," Drug Dev. Ind. Pharma., 28:631-639.
Rizzi et al., "Cyclic alternating pattern: a new marker of sleep alteration in patients with fibromyalgia?," Journal of Rheumatology, 31:1193-1199 (2004).
Rosa et al, "Automatic detection of cyclic alternating pattern (CAP) sequences in sleep: preliminary results," Clinical Neurophysiology, 110:585-592 (1999).
RX-s.net, https://web.archive.org/web/20060516153148/http:1/rx-s.net/weblog/more/cyclobenzaprine_flexerilreg/ [retrieved on Mar. 12, 2013], from 2006 (2 pages).
Santandrea et al., "A double-blind crossover study of two cyclobenzaprine regimens in primary fibromyalgia syndrome," Journal of International Medical Research, 21:74-80 (1993).
Shukla et al., "Mouth dissolving tablets I: an overview of formulation," Technology Scientia Pharmaceutica, 76:309-326. (2009).
Siddegowda et al., "Cyclo-benzaprinium chloride," Acta Crystallographica, Sect. E Struct. Rep. Online. Jul. 1, 2011; 67(Pt 7): o1846 (Abstract only) (2 pages).
Singh et al., "Tablet disintegrants: an Overview," American Journal of Pharmtech Research (2012) (10 pages).
Sutfin et al., "The analysis and disposition of imipramine and its active metabolites in man,". Psychopharmacology (Berl.), 82:310-317 (1984).
Telang et al., "Crystallization of D-mannitol in binary mixtures with NaCl: phase diagram and polymorphism," Pharmaceutical Research, 20:1939-1945 (2003).
Terzano et al., "Atlas, rules, and recording techniques for the scoring of cyclic alternating pattern sleep," Sleep Medicine, 3:187-199 (2002).
Terzano et al., "Polysomnographic analysis of arousal responses in obstructive sleep apnea syndrome by means of the cyclic alternating pattern," Journal of Clinical Neurophysiology, 13:145-155 (1996).
Thomas et al., "Sleep as a window into the world of fibromyalgia syndrome," Journal of Rheumatology, 38:2499-2500 (2011).
Till et al., "Evidence for route dependent biotransformation of cyclobenzaprine hydrochloride," Biopharmaceutics & Drug Disposition, 3:19-28 (1982).
Tukey et al., "Human UDP-glucuronosyltransferases: metabolism, expression, and disease," Annu Rev. Pharmacol. Toxicol., 40:581-616 (2000).
Vaddady et al., "In vitro pharmacokinetic/pharmacodynamic models in anti-infective drug development: focus on TB," Future Medicinal Chemistry, 2:1355-1369 (2010).
Vinar et al., "Proheptatriene in depression (extensive study)," Activitas Nervosa Superior, 7:290 (1965).
Wang et al., "Identification of human liver cytochrome P450 isoforms involved in the in vitro metabolism of cyclobenzaprine," Drug Metabolism and Disposition, 24:786-791 (1996).
Way et al., "Isotope dilution gas chromatographic-mass spectrometric measurement of tricyclic antidepressant drugs. Utility of the 4-carbethoxyhexafluorobutyryl derivatives of secondary amines," Journal of Analytical Toxicology, 22:374-382 (1998).
Winchell et al., "Cyclobenzaprine pharmacokinetics, including the effects of age, gender, and hepatic insufficiency," Journal of Clinical Pharmacology, 42:61-69 (2002).
Wong et al., "Potential interference of cyclobenzaprine and norcyclobenzaprine with HPLC measurement of amitriptyline and nortriptyline: resolution by GC-MS analysis," Journal of Analytical Toxicology, 19:218-224 (1995).
Yan et al., "Absolute bioavailability and stereoselective pharmacokinetics of doxepin," Xenobiotica., 32:615-623 (2002).
Yoshinari et al., "Moisture induced polymorphic transition of mannitol and its morphological transformation," International Journal of Pharmaceutics, 247(1-2):69-77 (2002).
Yoshinari et al., "The improved compaction properties of mannitol after a moisture-induced polymorphic transition," International Journal of Pharmaceutics, 258(1-2):121-131 (2003).
Zajc et al., "Physical properties and dissolution behaviour of nifedipine/mannitol solid dispersions prepared by hot melt method," International Journal of Pharmaceutics, 291:51-58 (2004).
Zelapar Full Prescribing Information, Cardinal Health, Inc., Valeant Pharmaceuticals North America, Jul. 2006 (2 pages).
Anxiety Disorders, Diagnostic and Statistical Manual of Mental Disorders, 4th Edition DSM-IV, American Psychiatric Association, pp. 393-444 (1994).
Donnelly, "Pharmacologic treatment approaches for children and adolescents with posttraumatic stress disorder," Child Adolescent Psychiatry Clinical North America, 12(2):251-269 (2003).
Evans, "Expert opinion: posttraumatic headaches among United States soldiers injured in Afghanistan and Iraq," Headache, 48(8):1216-1225 (2008).
Falcon et al., "Tricyclics: possible treatment for posttraumatic stress disorder," Journal of Clinical Psychiatry, 46(9):385-388 (1985).
Fietta et al., "Fibromyalgia and psychiatric disorders," Acta Biomed, 78(2):88-95 (2007).
Folstein et al., "Mini-mental state". A practical method for grading the cognitive state of patients for the clinician, Journal of Psychiatric Research, 12(3):189-198 (1975).
Ford et al., "Thermal Analysis of Sulphamethoxazole—Sugar Physical Mixes," Drug Development and Industrial Pharmacy, 11(5):1111-1112 (1985).
Greenblatt et al., "Use of Antipsychotics for the Treatment of Behavioral Symptoms of Dementia," Journal of Clinical Pharmacology, 56(9):1048-57 (2016).
Kar, "Behavioral and psychological symptoms of dementia and their management," Indian Journal of Psychiatry, 51(Suppl 1):S77-D86 (2009).
Miller et al., "Management of fibromyalgia, a distinct rheumatologic syndrome," Clinical Pharmacy, 6(10):778-786 (1987).
Pae, et al., "The relationship between fibromyalgia and major depressive disorder: a comprehensive review," Current Medical Research and Opinion, 24(8):2359-2371 (2008).
Pritchard et al., "Role of serotonin transporter polymorphisms in the behavioural and psychological symptoms in probable Alzheimer disease patients," Dementia and Geriatric Cognitive Disorders, 24(3):201-206 (2007).
Proitsi et al., "Association of serotonin and dopamine gene pathways with behavioral subphenotypes in dementia," Neurobiology of aging, 33(4):791-803 (2012).
Rose et al., "Correlates among nocturnal agitation, sleep, and urinary incontinence in dementia," American Journal of Alzheimer's Disease Other Dementia, 30(1):78-84 (2015).

(56) References Cited

OTHER PUBLICATIONS

Schneider et al., "Risk of death with atypical antipsychotic drug treatment for dementia: meta-analysis of randomized placebo-controlled trial," JAMA, 294(15):1934-43 (2005).

Shih et al., "Sundown Syndrome, Sleep Quality, and Walking Among Community-Dwelling People With Alzheimer Disease," Journal of the American Medical Directors Association, 18(5), 396-401 (2017).

Sura et al., "Dysphagia in the elderly: management and nutritional considerations," Clinical Interventions in Aging, 7:287-298 (2012).

Trzepacz et al., "Validation of the Delirium Rating Scale-revised-98: comparison with the delirium rating scale and the cognitive test for delirium," Journal of Neuropsychiatry and Clinical Neuroscience, 13(2):229-242 (2001).

Walsh, "Drugs Used to Treat Insomnia in 2002: Regulatory-Based Rather Than Evidence-Based Medicine," Sleep, 27(8):1441-1442 (2004).

Wang et al., "Prazosin for the treatment of behavioral symptoms in patients with Alzheimer disease with agitation and aggression," American Journal of Geriatric Psychiatry, 17(9):744-751 (2009).

Weintraub et al., "Pharmacologic interventions for psychosis and agitation in neurodegenerative diseases: evidence about efficacy and safety," Psychiatric Clinicals in North America, 28(4):941-983 (2005).

Williamson et al., "Pharmacological interventions for agitation in patients with traumatic brain injury: protocol for a systematic review and meta-analysis," Systemic Review, 5(1):193 (2016).

Wilson et al., "PTSD has Unreliable Diagnostic Criteria," Psychiatric Times, 26(7):4 pages (2009).

Xie et al., "Sleep drives metabolite clearance from the adult brain," Science, 342(6156):373-377 (2013).

Experimental Report, Batch No. #CYB_GAL_001, dated Aug. 24, 2020 (13 pages).

Gibson, "Pharmaceutical Preformulation and Formulation", 2nd Edition, New York, 231-234 (2009) (8 pages).

Mullin, "Crystallization and Precipitation," Ullman's Encyclopedia of Industrial Chemistry, 6th Edition, vol. 10, London 424-428 (2009) (16 pages).

Razaghi et al., "Investigation of cyclobenzaprine hydrochloride release from oral osmotic delivery systems containing a water-swellable polymer," Drug Development and Industrial Pharmacy, 28(6):695-701 (2002).

Rowe et al., "Handbook of Pharmaceutical Excipients," 6th Edition, London 424-428 (2009) (7 pages).

Bennet et al., "An internet survey of 2,596 people with fibromyaliga," BMC Muscluloskeletal Disorders, 8(27):2-12 (2007).

PTSD, Japanese Journal of Molecular Psychiatry, 2(3):39-45 (2002) (no translation).

Razaghi et al., "Investigation of cyclobenzaprine hydrochloride release from oral osmotic delivery systems containing a water-swellable polymer," Drug Development and Industrial Pharmacy, 28(6):631-639 (2002).

Razaghi et al., "Release of cyclobenzaprine hydrochloride from osmotically rupturable tablets," Drug Development and Industrial Pharmacy, 28(6):695-701 (2002).

Riumachi byougaku text [Rheumatology text], Japan, Shindan to Chiryo Sha, Inc., Sep. 10, 2010, pp. 410-412.

Ullmann's Encyclopedia of Industrial Chemistry, 6th Edition, Weinheim, vol. 10, Chapter 2 (16 Pages) (2003).

\* cited by examiner

EUTECTIC FORMULATIONS OF CYCLOBENZAPRINE HYDROCHLORIDE

RELATED APPLICATIONS

This application is a continuation of U.S. patent application Ser. No. 15/511,287, filed Mar. 15, 2017, which is a national stage application under 35 U.S.C. § 371 of International Application PCT/US2015/051068, filed on Sep. 18, 2015, which claims priority and benefit from U.S. Provisional Patent Application 62/052,238, filed Sep. 18, 2014, the contents and disclosures of which are incorporated by reference in their entireties.

BACKGROUND OF THE INVENTION

Cyclobenzaprine, or 3-(5H-dibenzo[a,d]cyclohepten-5-ylidene)-N,N-dimethyl-1-propanamine, was first approved by the U.S. Food and Drug Administration in 1977 for the treatment of acute muscle spasms of local origin. (Katz, W., et al., Clinical Therapeutics 10:216-228 (1988)).

Subsequent studies have shown cyclobenzaprine to also be effective in the treatment of fibromyalgia syndrome, post-traumatic stress disorder (PTSD), generalized anxiety disorder and depression. Furthermore, the utility of cyclobenzaprine as an agent for improving the quality of sleep, as a sleep deepener, or for treating sleep disturbances has been investigated. However, while FDA-approved therapeutics address pain and mood, there are currently no FDA-approved treatments that address the disturbed sleep and fatigue associated with fibromyalgia syndrome. Treatment with cyclobenzaprine may be particularly useful in treating sleep disturbances caused by, exacerbated by, or associated with fibromyalgia syndrome, prolonged fatigue, chronic fatigue, chronic fatigue syndrome, a sleep disorder, a psychogenic pain disorder, chronic pain syndrome (type II), the administration of a drug, autoimmune disease, stress or anxiety, or for treating an illness caused by or exacerbated by sleep disturbances, and symptoms of such illness. See, for example, U.S. Pat. Nos. 6,395,788 and 6,358,944, incorporated herein by reference.

Cyclobenzaprine HCl Active Pharmaceutical Ingredient (or API) is stable in pill, tablet or capsule formulations for oral administration when combined with certain excipients. However, Cyclobenzaprine HCl has slow absorption when ingested by mouth (per oral, or po). To speed absorption, tablets containing Cyclobenzaprine HCl have been formulated in various sublingual (SL) preparations. However, both sublingual and oral formulations can have issues with the stability of the API and the physical compositions themselves, especially when a basifying agent (a chemical compound that increases the pH of solutions after dissolution of Cyclobenzaprine HCl) is present. Therefore, a composition that increases stability of Cyclobenzaprine HCl (with or without the presence of a basifying agent), and methods of manufacturing such a composition, would be useful.

SUMMARY OF THE INVENTION

Some embodiments of the invention are:
1. A pharmaceutical composition comprising a eutectic of mannitol and Cyclobenzaprine HCl.
2. The pharmaceutical composition of claim 1, comprising 60%-90% Cyclobenzaprine HCl and 40%-10% mannitol by weight.
3. The pharmaceutical composition of claim 2, comprising amounts of Cyclobenzaprine HCl and mannitol selected from: 60%±2% Cyclobenzaprine HCl and 40%±2% mannitol, 65%±2% Cyclobenzaprine HCl and 35%+2% mannitol, 70%±2% Cyclobenzaprine HCl and 30%+2% mannitol, 75%±2% Cyclobenzaprine HCl and 25%±2% mannitol, 80%±2% Cyclobenzaprine HCl and 20%±2% mannitol, 85%±2% Cyclobenzaprine HCl and 15%±2% mannitol, and 90%±2% Cyclobenzaprine HCl and 10%±2% mannitol by weight.
4. The pharmaceutical composition of claim 3, comprising 75%±2% Cyclobenzaprine HCl and 25%±2% mannitol by weight.
5. The pharmaceutical composition of any one of claims 1-4, wherein the Cyclobenzaprine HCl:mannitol molar ratio is 1.76±0.1.
6. The pharmaceutical composition of any one of claims 1-5, wherein the Cyclobenzaprine HCl is micronized Cyclobenzaprine HCl.
7. The pharmaceutical composition of any one of claims 1-6, further comprising a basifying agent.
8. The pharmaceutical composition of claim 7, wherein the basifying agent is $K_2HPO_4$.
9. The pharmaceutical composition of claim 7, wherein the basifying agent is $Na_2HPO_4$.
10. The pharmaceutical composition of claim 7, wherein the basifying agent is trisodium citrate, anhydrous.
11. The pharmaceutical composition of any one of claims 1-10, wherein said composition comprises granules.
12. The pharmaceutical composition of claim 11, wherein said granules comprise cyclobenzaprine and mannitol.
13. The pharmaceutical composition of claim 12, wherein said mannitol is β mannitol and δ mannitol.
14. The pharmaceutical composition of any one of claims 11-13, wherein said granules comprise an inner layer comprising β mannitol and an outer layer comprising the eutectic of mannitol and Cyclobenzaprine HCl
15. A method of manufacturing a eutectic composition of any one of claims 1-14, comprising mixing Cyclobenzaprine HCl and mannitol.
16. The method of claim 15, wherein said mixing is wet granulation mixing.
17. The method of claim 15 or 16, further comprising mixing an alcohol with said Cyclobenzaprine HCl and said mannitol.
18. The method of claim 17, wherein said alcohol is methanol.
19. The method of claim 17, wherein said alcohol is ethanol.
20. The method of any one of claims 16-19, further comprising drying after said wet granulation.
21. The method of claim 20, wherein said wet granulation and drying are repeated one or more times.
22. The method of any one of claims 16-19, further comprising crystallization after said wet granulation.
23. The method of claim 22, wherein said wet granulation and crystallization are repeated one or more times.
24. A method of manufacturing a eutectic composition of any one of claims 1-14, comprising fluid bed drying Cyclobenzaprine HCl and mannitol
25. The method of any one of claims 15-24, wherein the eutectic composition comprises mannitol.
26. The method of claim 25, wherein the composition comprises Cyclobenzaprine HCl and the eutectic melts at 143.6±3° C.
27. The method of any one of claims 15-24, wherein the eutectic composition comprises δ mannitol.
28. The method of claim 27, wherein the composition comprises Cyclobenzaprine HCl and the eutectic melts at 134° C.±3° C.

DETAILED DESCRIPTION OF THE INVENTION

Figure 1:
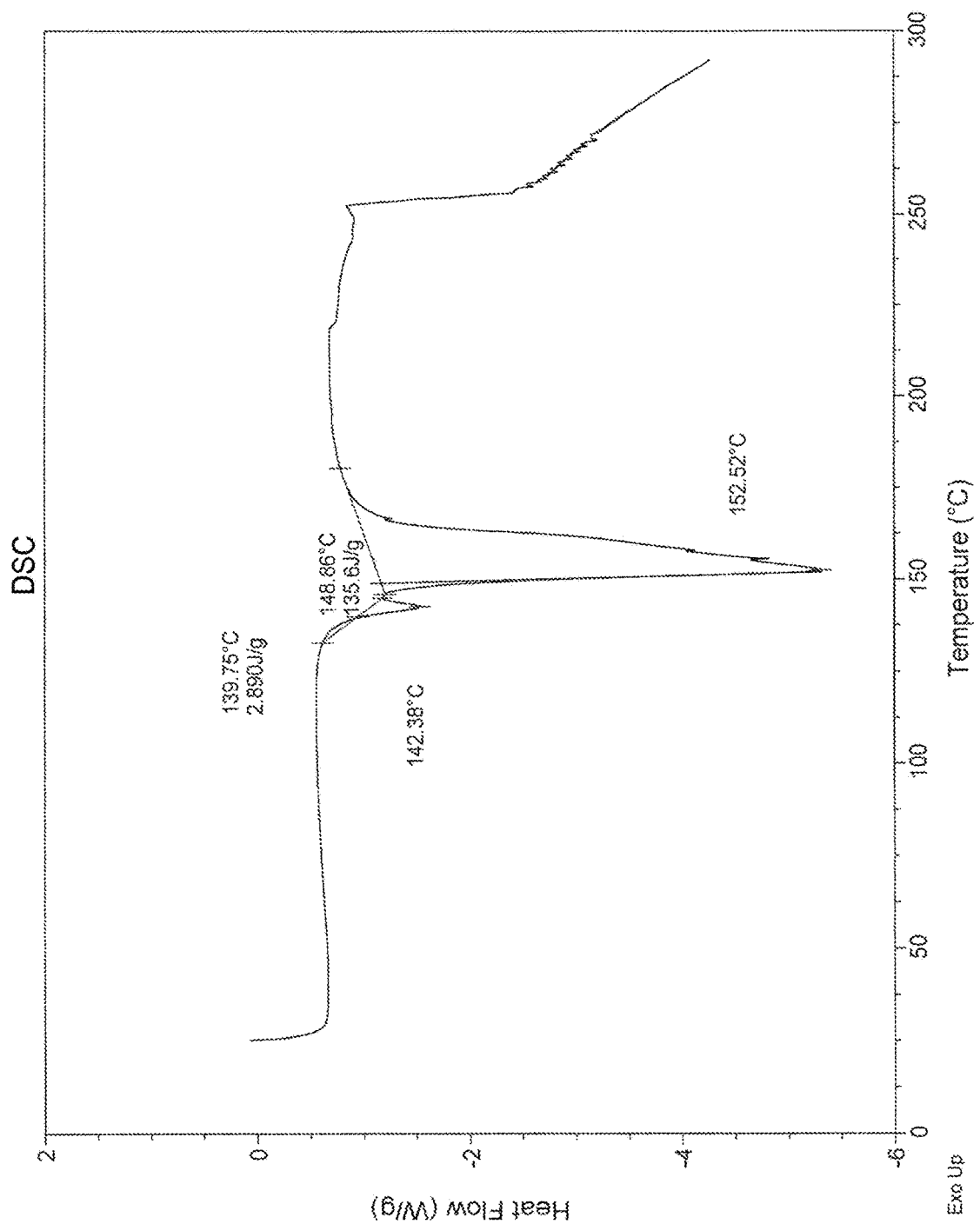
FIG. 1 depicts an exemplary differential scanning calorimetry (DSC) small peak for the δ mannitol eutectic (melting point of 139.75° C.) formed by wet granulation with cyclobenzaprine HCl, mannitol, and water.

Unless otherwise defined herein, scientific and technical terms used in this application shall have the meanings that are commonly understood by those of ordinary skill in the art. Generally, nomenclature used in connection with, and techniques of, pharmacology, cell and tissue culture, molecular biology, cell and cancer biology, neurobiology, neurochemistry, virology, immunology, microbiology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification.

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results include, but are not limited to, alleviation or amelioration of one or more symptoms associated with a disease or condition as described herein.

"Administering" or "administration of" a substance, a compound or an agent to a subject can be carried out using one of a variety of methods known to those skilled in the art. For example, a compound or an agent can be administered sublingually or intranasally, by inhalation into the lung or rectally. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

In solid drug product formulation, the knowledge of possible interactions between the drug substance and the excipients is a crucial point for the prediction of chemical and physical stability.

Very often the excipients can modify the biological activity and chemical stability of the API because the dissolution or chemical structures are changed. In some cases, the excipient can improve the chemical stability profile over time and avoid undesirable physical behavior of the final dosage form.

A eutectic system is a mixture of chemical compounds or elements that has a single chemical composition that melts at a lower temperature than any other composition made up of the same ingredients. A composition comprising a eutectic is known as the eutectic composition and its melting temperature is known as the eutectic temperature. To define a eutectic composition, a binary phase diagram should be built by analyzing different compounds ratios.

The effect of a eutectic on tablet properties shows that compaction provides the intimate contact and mutual solubility sufficient for eutectic formation. Eutectic compositions often have higher stability and/or dissolution rates than their non-eutectic counterparts. Because eutectics enhance dissolution, they can be employed to increase permeability in solid dispersions and dispersion systems. However, in the development of certain tableted dosage forms, undesired eutectic formation (during manufacturing operation such as wet granulation), can lead to unwanted changes in physical or chemical characteristics of the tablet, such as low eutectic melting temperature, sticking, unpredictable hardness, instability or difficulties in accelerated assessment of stability.

Mannitol and Sorbitol are excipients commonly used in solid drug products. Mannitol and Sorbitol are 6-carbon sugar alcohols isomers. Sugar alcohols are hydrogenated carbohydrates whose carbonyl group has been reduced to a primary or secondary hydroxyl group. Other 6-carbon sugar alcohols include Inositol, Galactitol, Fucitol, and Iditol.

Although Mannitol and Sorbitol can be included in pharmaceutical compositions, it is typically because they provide qualitative benefits such as sweet taste or a cooling effect in the mouth, but are physically inert. Thus, it was surprising to discover that mannitol formed a eutectic composition with Cyclobenzaprine HCl that resulted in tablets that had pharmaceutically acceptable stability even with a basifying agent. By contrast, sorbitol dissolved Cyclobenzaprine HCl upon heating (in a Differential Scanning calorimetry apparatus), did not form a eutectic, and resulted in tablets that disintegrated at room temperature with a basifying agent; underscoring the unpredictability of eutectic formation and the protective effect of the eutectic formed with mannitol. Without wishing to be bound by theory, it is possible that the two crystal lattices of mannitol and Cyclobenzaprine HCl co-penetrate and that this co-penetrating physical state provides protection of the Cyclobenzaprine HCl from hydration and other chemical interactions.

Compounds

The compound useful in embodiments of the present invention is Cyclobenzaprine HCl. In some embodiments, the compound is micronized. In alternative embodiments, the compound is not micronized. In some embodiments, the compound may be present in one or more crystal isoforms.

As used herein, "Cyclobenzaprine HCl" refers to the pharmaceutically acceptable cyclobenzaprine hydrochloride salt of cyclobenzaprine.

Eutectic Compositions

In some embodiments, the invention provides a pharmaceutical composition comprising a eutectic mixture of mannitol and an active pharmaceutical ingredient. In certain embodiments, the active pharmaceutical ingredient is Cyclobenzaprine HCl.

In some embodiments, the invention provides a pharmaceutical composition comprising a eutectic mixture of mannitol and Cyclobenzaprine HCl, e.g., a β mannitol eutectic, a δ mannitol eutectic, or a combination thereof. In certain embodiments (for example, when the composition comprises a β mannitol eutectic), the eutectic has a melting temperature of 143.6±3° C. In certain embodiments, a melting temperature of the eutectic is approximately 135.6° C., 136.6° C., 137.6° C., 138.6° C., 139.6° C., 140.6° C., 141.6° C., 142.6° C., 143.6° C., 144.6° C., 145.6° C., 146.6° C., 147.6° C., 148.6° C., 149.6° C., 150.6° C., 151.6° C., 152.6° C., or 153.6° C. In certain embodiments (for example, when the composition comprises a δ mannitol eutectic), the eutectic has a melting temperature of 134±3° C. In certain embodiments (for example, when the composition comprises a δ mannitol eutectic), a melting temperature of the eutectic is approximately 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., or 144° C. The skilled worker will appreciate that a measured melting temperature may vary based on the apparatus and conditions being used; however, control samples of β and δ mannitol easily can be used to distinguish between the melting temperatures of β and δ mannitol in a given sample. In particular embodiments, the melting temperature of the eutectic is the temperature at which melting begins. In alternative embodiments, the melting temperature of the eutectic is the temperature at which maximum melting is observed. In certain embodiments, the composition comprises greater than 5% Cyclobenzaprine HCl and less than 95% mannitol by weight. In certain embodiments, the composition comprises 1%-5% Cyclobenzaprine HCl and 99%-95% mannitol by weight. In certain embodiments, the composition comprises 5%-10% Cyclobenzaprine HCl and 95%-90% mannitol by weight. In certain embodiments, the composition comprises 10%-20% Cyclobenzaprine HCl and 90%-80% mannitol by weight. In certain embodiments, the composition comprises 10%-90% Cyclobenzaprine HCl and 90%-10% mannitol by weight, for example, 60%-90% Cyclobenzaprine HCl and 40%-10% mannitol or 70%-80% Cyclobenzaprine HCl and 30%-20% mannitol by weight. Exemplary compositions comprise 60%±2% Cyclobenzaprine HCl and 40%±2% mannitol, 65%±2% Cyclobenzaprine HCl and 35%±2% mannitol, 70%±2% Cyclobenzaprine HCl and 30%±2% mannitol, 75%±2% Cyclobenzaprine HCl and 25%±2% mannitol, 80%±2% Cyclobenzaprine HCl and 20%±2% mannitol, 85%±2% Cyclobenzaprine HCl and 15%±2% mannitol, and 90%±2% Cyclobenzaprine HCl and 10%±2% mannitol by weight. In certain embodiments (e.g., a composition comprising a β mannitol eutectic), a composition comprises 75%±10% Cyclobenzaprine HCl and 25%±10% mannitol by weight. In certain embodiments, a composition comprises 75%±2% Cyclobenzaprine HCl and 25%±2% mannitol by weight. In certain embodiments, a composition comprises 75% Cyclobenzaprine HCl and 25% mannitol by weight. In certain embodiments (e.g., a composition comprising a δ mannitol eutectic), a composition comprises 65%±10% Cyclobenzaprine HCl and 35%±10% mannitol by weight. In certain embodiments, a composition comprises 65%±2% Cyclobenzaprine HCl and 35%±2% mannitol by weight. In certain embodiments, a composition comprises 65% Cyclobenzaprine HCl and 35% mannitol by weight. In certain embodiments, the composition comprises Cyclobenzaprine HCl and mannitol in a Cyclobenzaprine HCl:mannitol molar ratio of 1.70±0.1 to 1.80±0.1. In certain embodiments, the molar ratio is about 1.6 to 2.0. In particular embodiments, the molar ration is 1.70±0.1, 1.71±0.1, 1.72±0.1, 1.73±0.1, 1.74±0.1, 1.75±0.1, 1.76±0.1, 1.77±0.1, 1.78±0.1, 1.79±0.1, or 1.80±0.1. In certain embodiments, the molar ratio is 1.60±0.5, 1.65±0.5, 1.70±0.5, 1.75±0.5, 1.80±0.5, 1.85±0.5, 1.90±0.5, 1.95±0.5, or 2.0±0.5. In certain embodiments the molar ratio is 1.76±0.1. In certain embodiments the molar ratio is 1.76±0.5.

In certain embodiments, additional mannitol is added to the eutectic, e.g., as a diluent or as a component of an explosant (an agent that facilitates disintegration in the oral cavity, such as Pearlitol® Flash). In these embodiments, the total amount of mannitol will be higher than the amount of mannitol present in the eutectic as originally formed. For example, when additional mannitol is added, the composition can comprise approximately 90% by weight, approximately 85% by weight, approximately 80% by weight, approximately 75% by weight, approximately 70% by weight, approximately 65% by weight, approximately 60% by weight, or approximately 55% by weight of mannitol. An exemplary composition with added mannitol is:

| Component | Commercial Name | Function | mg/tab | g/Batch |
|---|---|---|---|---|
| Eutectic by Wet Granulation | N/A | Active Ingredient | 13.4 (Corresponding to 10 mg of Cyclobenzaprine HCl) | 87.1 |
| Mannitol SD200 | Pearlitol SD200 | Diluter | 68.0 | 442.0 |
| Crospovidone | Kollidon CL | Disintegrant agent | 16.5 | 107.25 |
| Colloidal Silica | Aerosil 200 | Glidant agent | 1.5 | 9.75 |
| Sodium Stearyl Fumarate | Lubrisanaq | Lubricant | 0.6 | 3.9 |
| | | Total Weight | 100.0 mg | 650.0 g |

Another benefit of the eutectic compositions of the invention is increased stability of a tablet containing Cyclobenzaprine HCl. In some embodiments, the invention provides a pharmaceutical composition comprising Cyclobenzaprine HCl and mannitol, wherein the composition has an increased stability in tablet form as compared to the same tablet without mannitol, e.g., to a tablet comprising sorbitol but not mannitol. Indeed, a tablet containing Cyclobenzaprine HCl, $K_2HPO_4$, and mannitol was stable for three months at 40° C. and 75% relative humidity. By contrast, a tablet containing Cyclobenzaprine HCl, $K_2HPO_4$, and sorbitol stored at the same conditions disintegrated before reaching even reaching one week.

In some embodiments, the invention provides a pharmaceutical composition comprising Cyclobenzaprine HCl and mannitol, wherein the composition has an increased dissolution rate of a stable tablet compared to Cyclobenzaprine HCl alone or in a formulation containing one or more excipients that are not basifying agents. For example, the composition at 5 minutes can exhibit 100%, greater than 95%, greater than 90%, greater than 85%, greater than 80%, greater than 75%, greater than 70%, greater than 65%, greater than 60%, greater than 55%, greater than 50%, greater than 45%, greater than 40%, greater than 35%, greater than 30%, or greater than 25% dissolution when mixed with 100 mL of 50 mM Citrate pH 4 at 37.0±0.5° C. For example, the composition at 10 minutes can exhibit 100%, greater than 95%, greater than 90%, greater than 85%, greater than 80%, greater than 75%, greater than 65%, greater than 60%, greater than 55%, greater than 50%, dissolution when mixed with 100 mL of 50 mM Citrate pH 4 at 37.0±0.5° C. For example, the composition at 240 minutes can exhibit 100%, greater than 95%, greater than 90%, greater than 85%, greater than 80%, greater than 75%, greater than 65%, greater than 60%, greater than 55%, greater than 50%, dissolution when mixed with 100 mL of 50 mM Citrate pH 4 at 37.0±0.5° C. For very soluble compounds (e.g., Cyclobenzaprine HCl), a continuous flow dissolution apparatus can be used to measure dissolution.

Mannitol is capable of crystallizing in three polymorphic states: α, β, and δ. These three forms can be distinguished by X-ray powder diffraction, and each polymorph has a different melting point. See, e.g., Sharma and Kalonia, AAPS PharmaSciTech 5(1):E10 (2004). Even more surprising than the observation of a first eutectic with Cyclobenzaprine HCl and mannitol (β polymorph) was the observation of a second eutectic with a different polymorphic form of mannitol (δ polymorph). The eutectic comprising δ mannitol and Cyclobenzaprine HCl (also referred to herein as the "δ mannitol eutectic") has several advantages over the eutectic comprising mannitol and Cyclobenzaprine HCl (also referred to herein as the "β mannitol eutectic"). Prime among these are a lower melting point than the β mannitol eutectic and enhanced dissolution over the β mannitol eutectic. Another advantage is greater stability in pharmaceutical compositions (including tablets) than the β mannitol eutectic including compositions that contain a basifying agent. Yet another advantage is greater local tolerability in pharmaceutical compositions (including tablets) than the β mannitol eutectic including compositions that contain a basifying agent. Improved dissolution and conversion to cyclobenzaprine free base also should improve tolerability, including reduced transient numbing of the tongue during administration of a tablet under the tongue to improve sublingual absorption.

In some embodiments, the invention provides a eutectic pharmaceutical composition comprising Cyclobenzaprine HCl and mannitol, wherein the mannitol is in its β polymorphic state. In some embodiments, the invention provides a eutectic pharmaceutical composition comprising Cyclobenzaprine HCl and mannitol, wherein the mannitol is in its δ polymorphic state. In certain embodiments, the pharmaceutical composition comprising the mannitol in its β polymorphic state is a sublingual composition. In certain embodiments, the pharmaceutical composition comprising the mannitol in its β polymorphic state is an oral composition. In certain embodiments, the pharmaceutical composition comprising the mannitol in its δ polymorphic state is a sublingual composition. In certain embodiments, the pharmaceutical composition comprising the mannitol in its δ polymorphic state is an oral composition. In particular embodiments wherein the composition is an oral composition, the oral composition is bioequivalent to 5 mg Cyclobenzaprine HCl oral tablets (e.g., Flexeril 5 mg). In particular embodiments wherein the composition is an oral composition, the oral composition is bioequivalent to 10 mg Cyclobenzaprine HCl oral tablets (e.g., Flexeril 10 mg). Flexeril tablets are composed of hydroxypropyl cellulose, hydroxypropyl methylcellulose, iron oxide, lactose, magnesium stearate, starch, and titanium dioxide. Dosing 10 mg t.i.d. in normal healthy volunteers, the AUC at steady state (after 4 days of dosing) was 177 ng·hr/mL (range, 80-319 ng·hr/mL) and the Cmax was 25.9 ng/mL (range, 12.8-46.1 ng/mL). Additional pharmacokinetic properties of orally administered Cyclobenzaprine can be found, for example, in Winchell et al., J Clin Pharmacol. 42(1):61-9 (2002) and Hucker et al., J Clin Pharmacol. 17(11-12):719-27 (1977).

In some embodiments, the invention provides a composition comprising eutectic of mannitol and Cyclobenzaprine HCl. The skilled worker will understand that these compositions may be suitable for administration in a variety of ways, such as those described herein. For example, a composition may be suitable for administration orally (administration wherein the Cyclobenzaprine is absorbed in the gastrointestinal tract), or for transmucosal absorption (e.g., sublingual, buccal, or intranasal absorption, or by inhalation).

In some embodiments, the invention provides a composition that is a granulate composition. In certain embodiments, the granules are granules comprising cyclobenzaprine HCl and mannitol. In particular embodiments, the granules comprise an excess of mannitol. In more particular embodiments, the granules comprise β mannitol, δ mannitol, or both. Granules comprising an excess of mannitol, in particular, may contain both β mannitol and δ mannitol. For example, a granule produced by a method such as fluid bed drying may comprise an inner layer of β mannitol and an outer layer of δ mannitol-cyclobenzaprine eutectic.

Methods of Manufacturing Eutectic Compositions

The skilled worker will appreciate that a eutectic composition of the invention can be manufactured according to any of a number of known methods. In some embodiments, the invention provides methods for producing a eutectic composition of the invention comprising milling an API (Cyclobenzaprine HCl) with mannitol, mixing an API (Cyclobenzaprine HCl) with mannitol, or a combination thereof. For example, the API and mannitol can be milled in an agate mortar or mixed in a high shear granulator. High shear mixing combines dry powders using a high speed impellor and chopper blades to uniformly mix the ingredients. Some particle size reduction is possible due to the shear force and the high speed of the mixing blades. The API and mannitol also can be milled and mixed in, for example, a Turbula® Shaker-Mixer. In certain embodiments, the API and mannitol can be mixed via compression, for example, via roller compaction. Roller compaction forces fine powders between two counter-rotating rolls and presses the raw materials into a solid compact or sheet (referred to as flakes). The flakes are reduced in size until they reach a desired grain size. In certain embodiments, mannitol can be melted and mixed with Cyclobenzaprine HCl to form a eutectic composition. In certain embodiments, the API is a micronized API (e.g., micronized Cyclobenzaprine HCl).

In some embodiments, the invention provides methods for producing a eutectic composition of the invention comprising spray drying a solution of an API (Cyclobenzaprine HCl) with mannitol. The skilled worker will appreciate that spray drying is routine, and parameters for spray drying can be determined without undue experimentation. For example, spray drying can be performed under any of the following conditions:

T Inlet (° C.): 120-150
T Outlet (° C.): 73-90
Feed rate (ml/min): 4-6
Flow Rate (L/h): 600-800
Aspiration (100%): 100
delta Pressure (mbar): 2-20

These conditions also may be scaled up or modified to provide higher throughput manufacturing.

In some embodiments, a composition comprising a δ mannitol eutectic of cyclobenzaprine HCl and mannitol is produced by mixing mannitol and cyclobenzaprine HCl. This mixing can be, for example, wet granulation, including high shear wet granulation. FIG. 1 shows an exemplary differential scanning calorimetry (DSC) small peak for the δ mannitol eutectic (melting point of 139.75° C.) formed by wet granulation with cyclobenzaprine HCl, mannitol, and water. Wet granulation can be followed by fluid bed drying, and optionally milling, to produce the composition. Without wishing to be bound by theory, during wet granulation it is possible that cyclobenzaprine and mannitol (which starts in its β form) become metastable and then some or all of the wet edges of β mannitol crystals in the paste formed by wet granulation crystallize into the β and/or δ mannitol eutectic with Cyclobenzaprine HCl. This may occur as the solvent evaporates and the processes of crystal co-penetration and re-crystallization into the eutectics happens during the mixing phase or the drying phase, either directly or through a metamorphic metastable amorphous intermediate and subsequent nucleation with the β and/or δ mannitol eutectic. In some embodiments, wet granulation and drying can be performed in iterative cycles to stimulate or enhance the formation of a δ mannitol eutectic. Without wishing to be bound by theory, performing wet granulation and drying in cycles may enhance the formation of a δ mannitol eutectic because, while an individual cycle may produce a fraction of the total δ mannitol eutectic possible, each cycle helps propagate the formation of additional δ mannitol.

In some embodiments, a composition comprising a δ mannitol eutectic of cyclobenzaprine HCl and mannitol is produced by fluid bed drying (also known as fluidized bed drying). Without wishing to be bound by theory, fluid bed drying may have advantages over other methods of eutectic formation because it provides controlled, gentle and even drying of wet solids. The intensive heat/mass exchange of the fluidized bed product makes this method particularly effective and time-saving. The technology is also suitable for post-drying of spray granulated or extruded products with very low residual moisture.

In certain embodiments, fluid bed drying can be used in the formation of a cyclobenzaprine drug product. The drying process with fluid bed drying can reduce the drying time in the drying oven approximately twenty-fold over other methods. In addition, fluid bed drying provides controlled and uniform drying conditions compared to potentially uneven drying in trays. Moreover, fluid bed drying can improve homogeneous distribution of an active pharmaceutical ingredient on the surface of one or more excipients.

Fluid bed drying technology can be used when a liquid solution containing a solubilized drug substance (e.g., cyclobenzaprine HCl) is sprayed on the surface of excipient particles. In this way, the nebulized solution on the excipient particle surfaces creates a positive interaction between the solution and the solid particles. During the drying step under hot air flow, water is removed from the surface and the active pharmaceutical ingredient links to the excipient particle. In some embodiments, a cyclobenzaprine HCl solution (e.g., cyclobenzaprine HCl and water) is sprayed onto mannitol, forming a eutectic between the cyclobenzaprine and mannitol. Without wishing to be bound by theory, when a solution of an active pharmaceutical ingredient (e.g., cyclobenzaprine HCl) is spread by a nozzle on the surface, and a eutectic forms, the eutectic particles may physically interact with particles comprising one or more excipients, creating granules with desirable dimensions.

Another advantage of fluid bed drying is that drying takes place in a thermodynamic equilibrium. The inlet air temperature is selected such that only as much moisture evaporates from the surface of the granulate as is transported through the capillaries from the interior of the granulate to the surface. During this moisture migration, the active pharmaceutical ingredient can link to the substance on which it has been sprayed. For example, when cyclobenzaprine HCl is sprayed onto mannitol, the cyclobenzaprine HCl and mannitol mix in the correct ratio to form a eutectic, even though there is an excess of mannitol not needed for eutectic formation. Even more surprisingly, this process produced a eutectic of cyclobenzaprine and δ mannitol even though the mannitol on which the cyclobenzaprine HCl was β mannitol. Properly used, fluidized bed drying provides an efficient solution to create an appropriate granule particle size for good tableting with even active pharmaceutical ingredient distribution throughout the tablet and without undesired crumbling.

Figure 2:
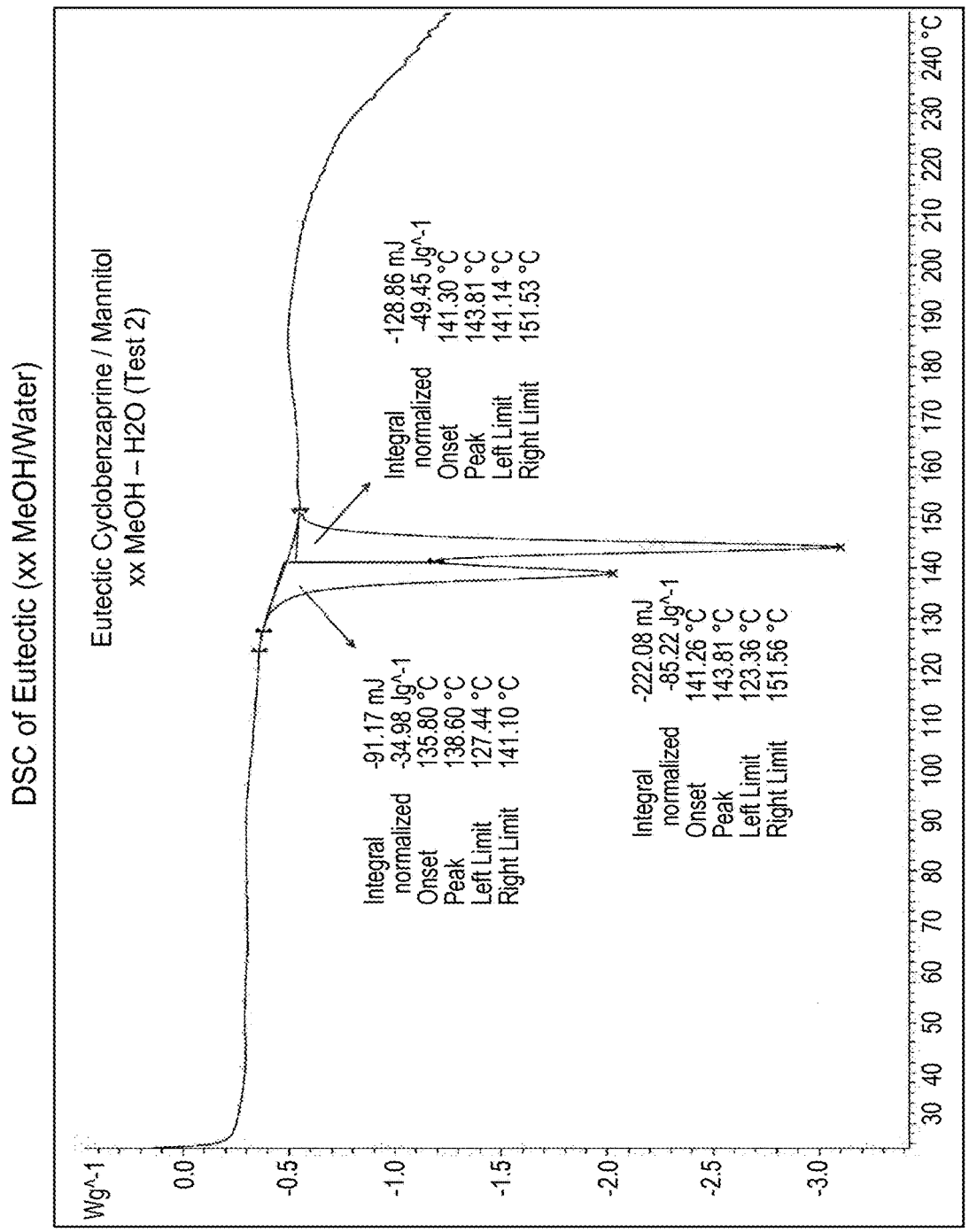
FIG. 2 depicts a differential scanning calorimetry curve of a δ mannitol eutectic formed by dissolving cyclobenzaprine and mannitol in a mixture of methanol and water, followed by rapid evaporation.
Figure 3:
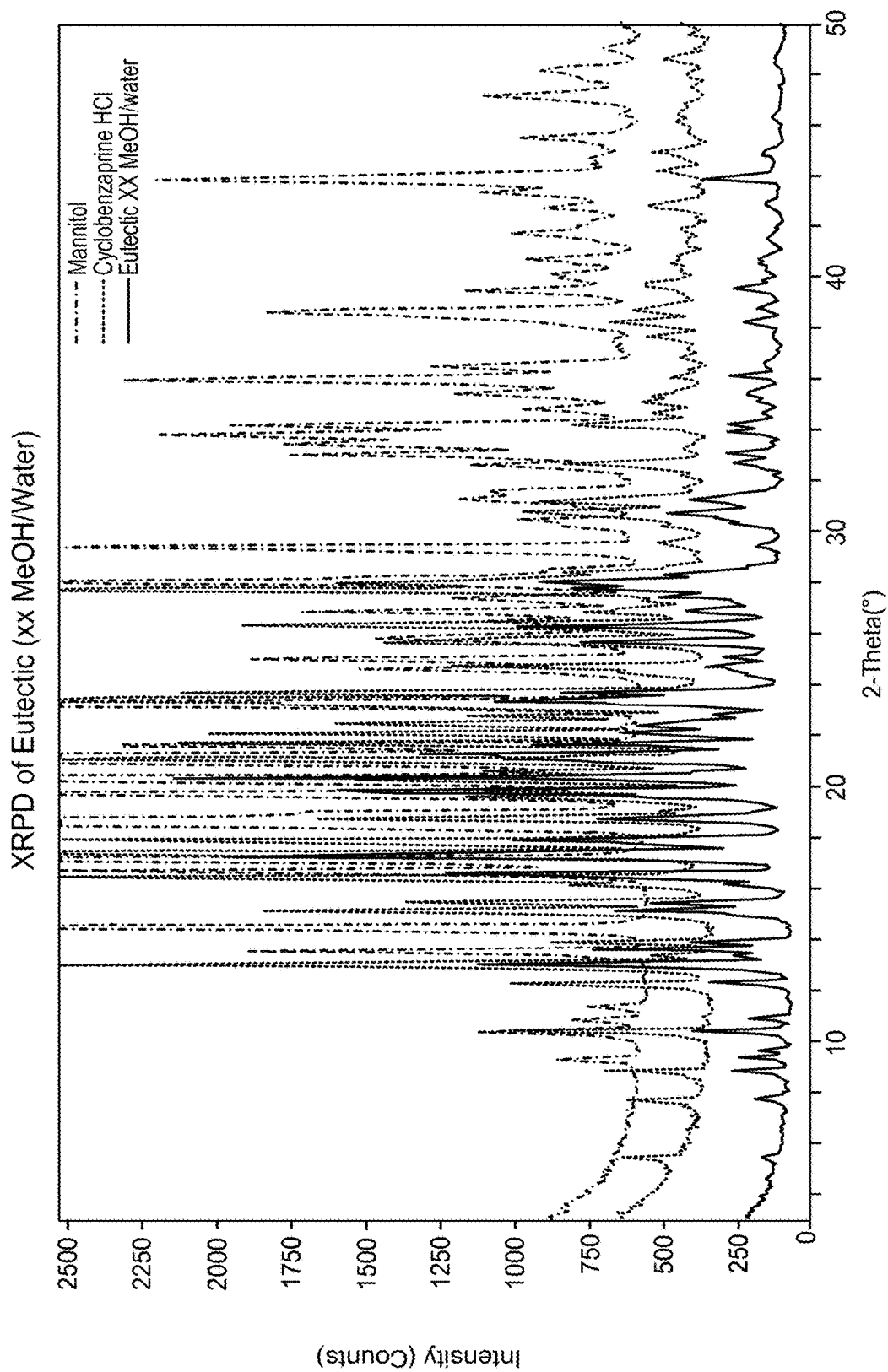
FIG. 3 depicts an x-ray powder diffraction pattern of a δ mannitol eutectic formed by dissolving cyclobenzaprine and mannitol in a mixture of methanol and water, followed by rapid evaporation.
Figure 4:
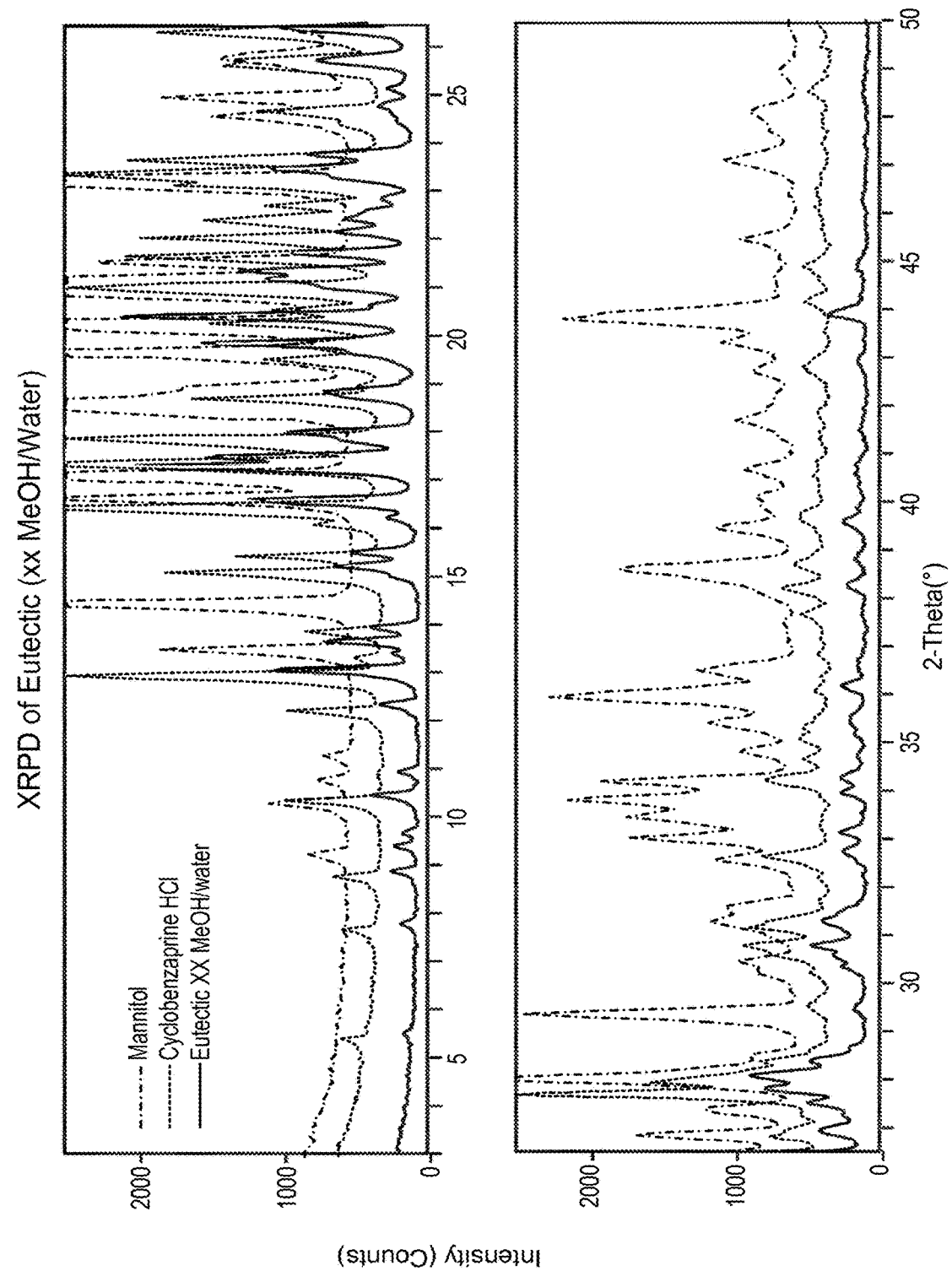
FIG. 4 depicts X-ray powder diffraction data for a δ mannitol eutectic formed by dissolving cyclobenzaprine and mannitol in a mixture of methanol and water, followed by rapid evaporation.
Figure 9:
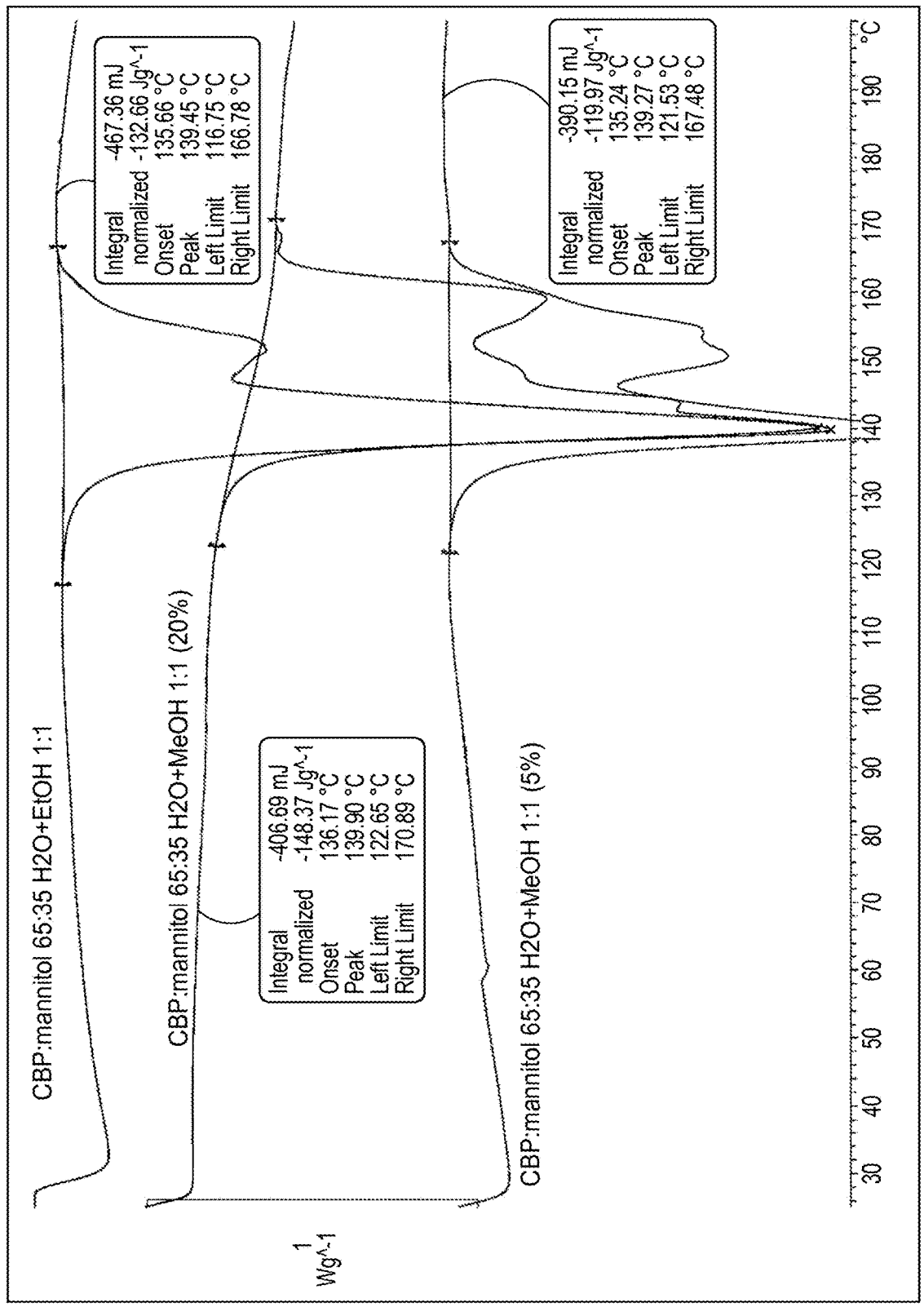
FIG. 9 depicts a differential scanning calorimetry curve for a δ mannitol eutectic formed from a 65% cyclobenzaprine:35% mannitol (w/w) mixture that underwent rapid evaporation in a 1:1 mixture of methanol:water.
Figure 10:
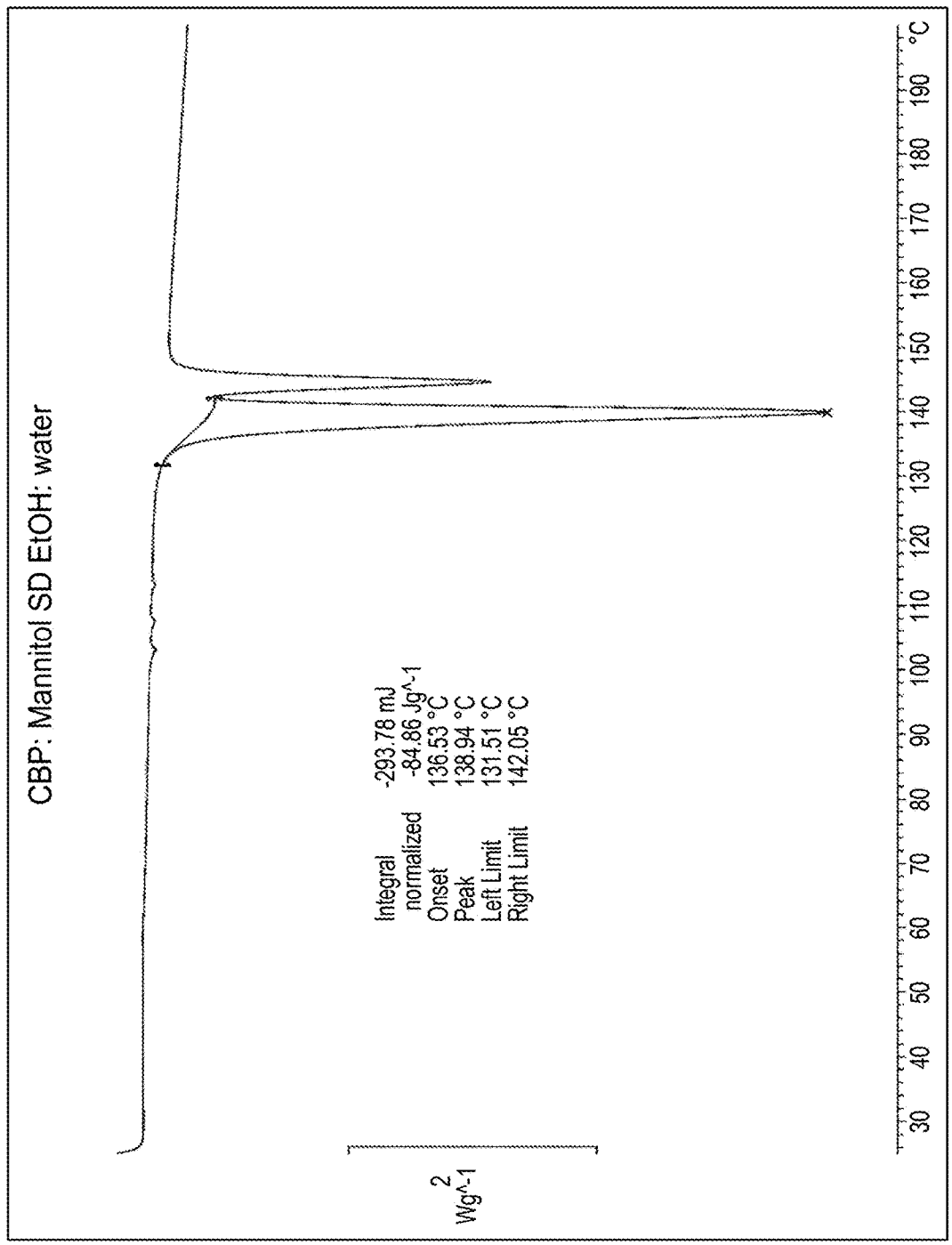
FIG. 10 depicts differential scanning calorimetry data for a cyclobenzaprine HCl-mannitol mixture that was spray dried with ethanol and water.
Figure 11:
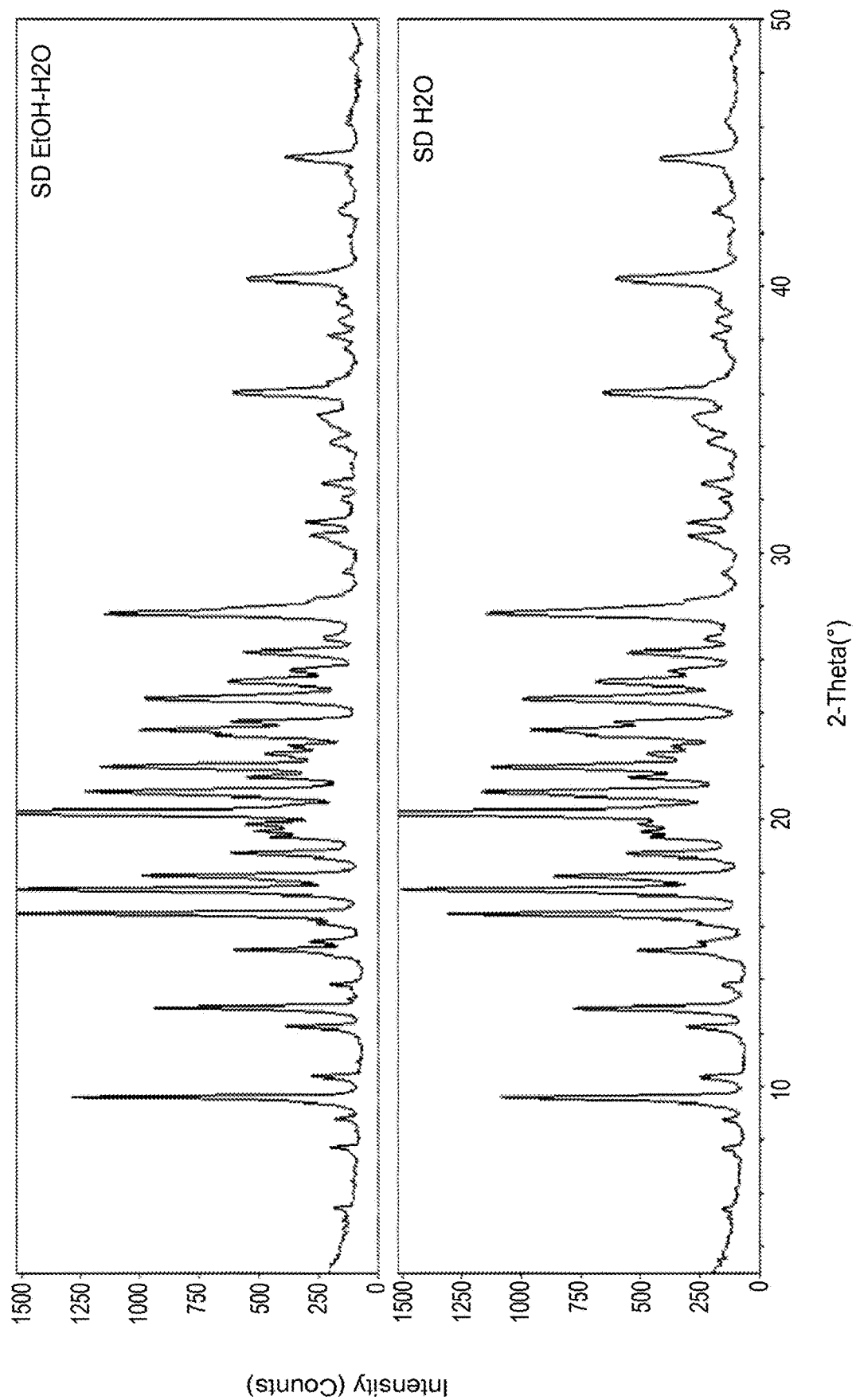
FIG. 11 depicts X-ray powder diffraction data comparing a cyclobenzaprine HCl-mannitol mixture that was spray dried with ethanol and water (top) and spray drying with water alone (bottom).

In some embodiments, an alcohol is used to stimulate or enhance the formation of a δ mannitol eutectic. Exemplary alcohols include, but are not limited to, ethanol, methanol, and isopropanol. In certain embodiments, ethanol is used to stimulate or enhance the formation a δ mannitol eutectic in combination with spray drying (see FIG. 10 for differential scanning calorimetry data and FIG. 11 for X-ray powder diffraction data comparing spray drying with ethanol and water and spray drying with water alone). For example, a 1:1 ethanol:water mixture with 5% (w/w) of a mixture of cyclobenzaprine and mannitol can be introduced during spray drying to create a δ mannitol eutectic. In alternative embodiments, ethanol is used to stimulate or enhance the formation a δ mannitol eutectic in combination with wet granulation mixing. In yet other embodiments, ethanol is used to stimulate or enhance the formation a δ mannitol eutectic in combination with freeze drying. In still other embodiments, ethanol is used to stimulate or enhance the formation a δ mannitol eutectic in combination with rapid evaporation. In still additional embodiments, ethanol is used to stimulate or enhance the formation a δ mannitol eutectic in combination with fluid bed drying. In certain embodiments, methanol is used to stimulate or enhance the formation a δ mannitol eutectic in combination with spray drying. In alternative embodiments, methanol is used to stimulate or enhance the formation a δ mannitol eutectic in combination with wet granulation mixing. In yet other embodiments, methanol is used to stimulate or enhance the formation a δ mannitol eutectic in combination with freeze drying. In still other embodiments, methanol is used to stimulate or enhance the formation a δ mannitol eutectic in combination with rapid evaporation. In still additional embodiments, methanol is used to stimulate or enhance the formation a δ mannitol eutectic in combination with fluid bed drying. An exemplary protocol for spray drying to obtain a δ mannitol eutectic via spray drying with ethanol is as follows:
Equipment: Buchi Mini Spry Dryer SD B 290
Ethanol:water solvent in the ratio 1:1 v/v
Cyclobenzaprine:mannitol mixture (at a ratio of, for example, 65:35) concentration in the solution: 5% w/w
Spray drying conditions:
Inlet temperature=150° C.
Outlet temperature=90° C.
Solution flow rate=c.a 6 mL/min
Delay time before removing the powder from the equipment (requested for the complete recrystallization of the powder distributed on the equipment)=1-2 hours In some embodiments, a process of rapid evaporation is used to stimulate or enhance the formation of a δ mannitol eutectic. Rapid evaporation refers to the mixture of cyclobenzaprine HCl and mannitol with a solvent (e.g., water or a mixture of water and an alcohol such as methanol or ethanol) followed by a step in which the solvent is quickly evaporated, e.g., by passing hot air over the solution. The cyclobenzaprine HCl, mannitol, and water can be mixed to form a paste (as in wet granulation) or can be mixed to form a solution. By way of example, a 65% cyclobenzaprine:35% mannitol (w/w) mixture that has undergone rapid evaporation in a 1:1 mixture of methanol:water (final concentration of the cyclobenzaprine/mannitol mixture between 5% and 20%) forms a δ mannitol eutectic after approximately 30 minutes of drying (see FIG. 9). See also FIGS. 2-4 for δ mannitol eutectic formed by dissolving cyclobenzaprine and mannitol in a mixture of methanol and water, followed by rapid evaporation.

Figure 5:
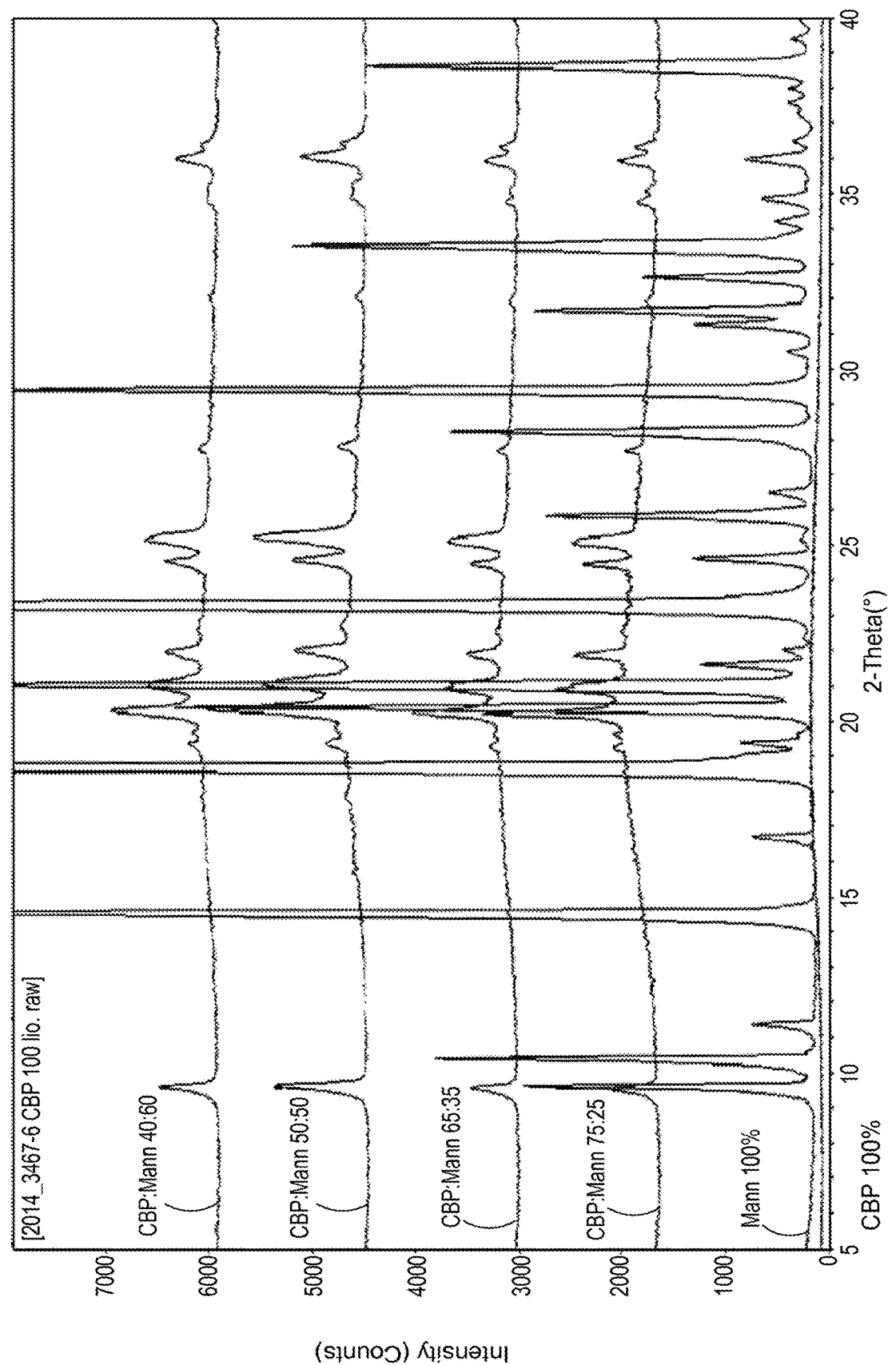
FIG. 5 depicts X-ray powder diffraction data for a δ mannitol eutectic formed by freeze drying without annealing.
Figure 6:
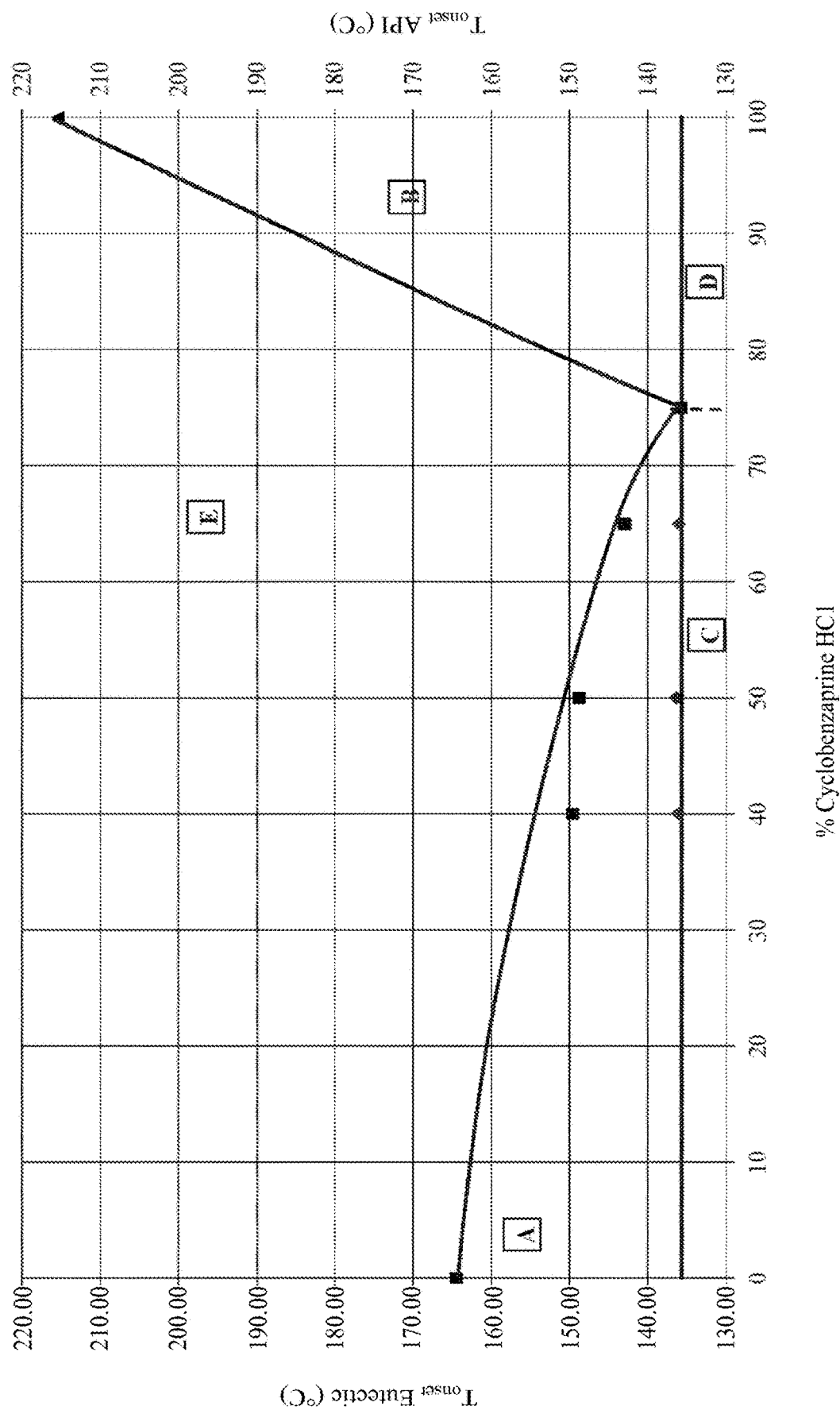
FIG. 6 depicts a phase diagram for a δ mannitol eutectic formed by freeze drying without annealing.
Figure 7:
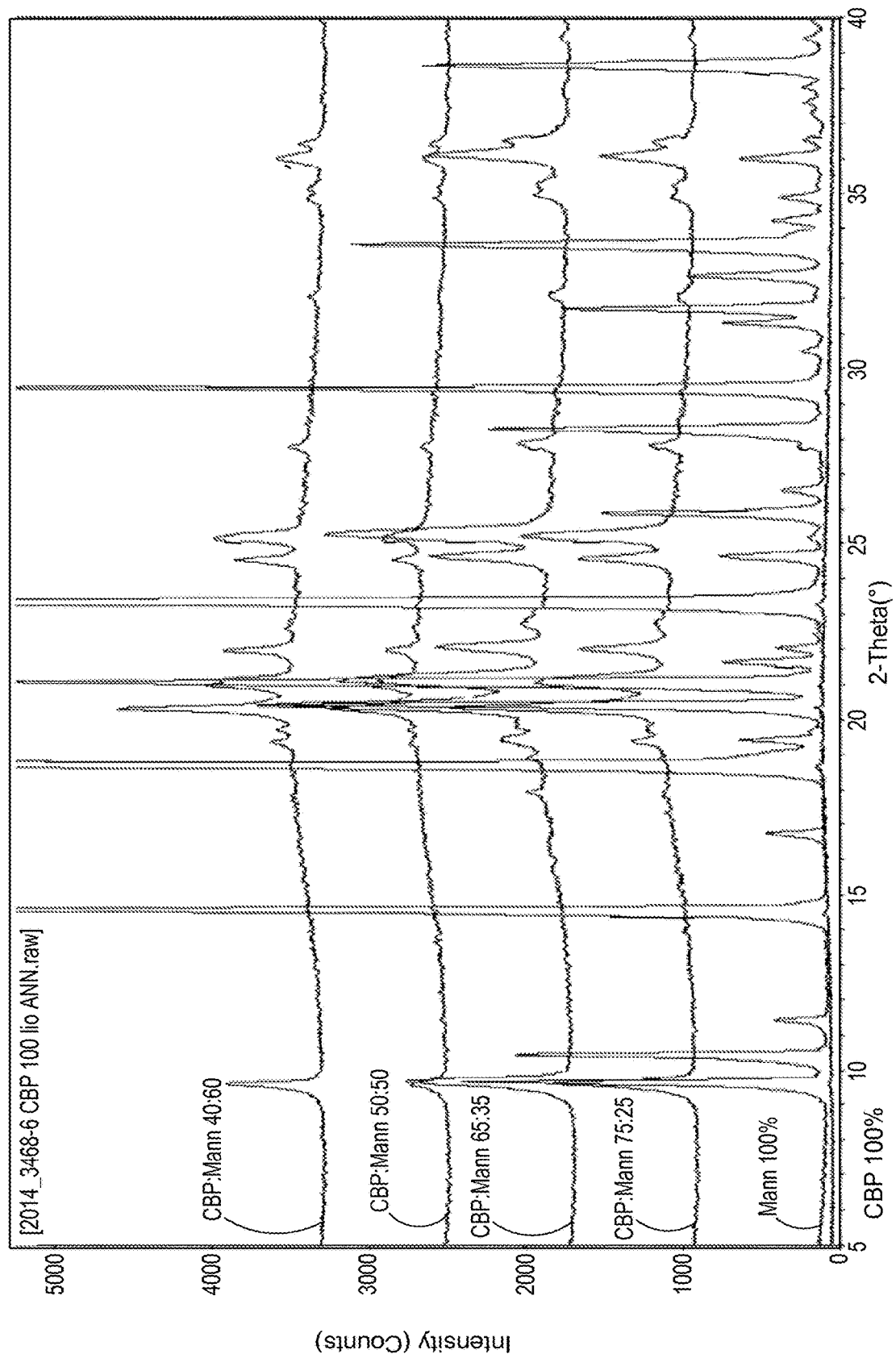
FIG. 7 depicts X-ray powder diffraction data for a δ mannitol eutectic formed by freeze drying with annealing.
Figure 8:
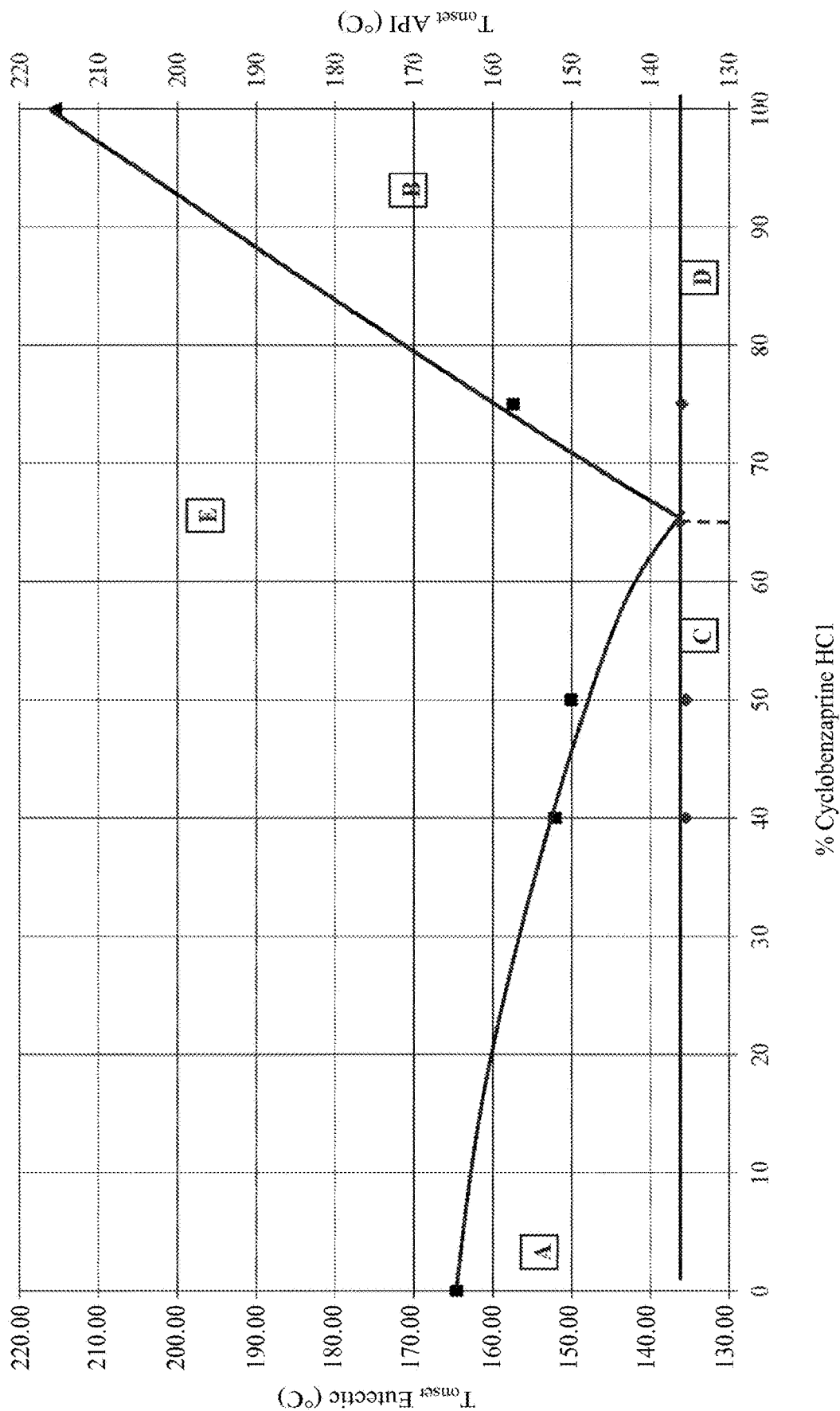
FIG. 8 depicts a phase diagram for a δ mannitol eutectic formed by freeze drying with annealing.

In some embodiments, freeze drying is used to stimulate or enhance the formation of a δ mannitol eutectic. In certain embodiments, the freeze drying is performed without annealing. See FIGS. 5 and 6, which show X-ray powder diffraction data and a phase diagram, respectively, for a δ mannitol eutectic formed by freeze drying without annealing. Although these traces show low crystallinity in the initial composition, after a period of crystallization, δ mannitol eutectic crystals more clearly formed. In alternative embodiments, the freeze drying is performed with annealing. See FIGS. 7 and 8, which show X-ray powder diffraction data and a phase diagram, respectively, for a δ mannitol eutectic formed by freeze drying with annealing. Although these traces show low crystallinity in the initial composition, after a period of crystallization, δ mannitol eutectic crystals more clearly formed.

Methods of Detecting Eutectic Compositions

Methods of detecting eutectic compositions are well known. The skilled worker will appreciate that eutectic compositions can be detected by any of these methods. For example, rapid differential scanning calorimetry ("DSC") can be used to detect a eutectic melting point by evaluating the amount of heat recorded from eutectic melting and comparing it with the melting heat of the eutectic composition. During a slow scan of DSC, the increased temperature in the crucible facilitates the formation of the eutectic even when the two components (such as Mannitol and cyclobenzaprine HCl may not have been mixed before the start of the experiment.) In contrast, a rapid DSC scan reduces the time during which eutectic compositions can form in the crucible because the temperature inside the crucible rapidly increases during the analysis and rapidly reaches the values at which the mannitol melts. Another useful method is measuring compaction force vs. DSC eutectic melting point. In this method, mixtures are prepared with known ratios and then submitted to well-defined compaction forces. DSC analyses are then performed and the heat of the eutectic melting versus the forces is then recorded and plotted. These values are compared with those obtained with the eutectic ratio, providing the percentage of eutectic in the formulation.

An additional method that can be used to detect the amount of eutectic in a composition is to compare tensile strength and compression force. In this method, tablets are prepared with only mannitol and API at different compression forces. For each tablet prepared, the percentage of eutectic formed versus tensile strength of the tablets is correlated. There is a proportionally linear correlation between the tensile strength and the intimate contact area. The slope of this correlation provides the percentage of the eutectic formed.

There is a linear correlation between the percentage of eutectic composition in a preparation and the porosity of powders in a composition. In this method, a standard curve can be generated by preparing samples with different ratios of components in which at least one of the components has a variety of different particle sizes, measuring the specific surface area and the porosity of the powders and plotting porosity against the percentage of eutectic. Because there is a linear correlation between the two parameters, the slope of this correlation with what is recorded for the eutectic mixture provides the percentage of the eutectic formed Dissolution rate also can be used to detect the percent of eutectic because a eutectic may have higher dissolution and higher bioavailability. In this method, the intrinsic dissolution rate (using disk sample holder in a defined and appropriate medium) of the single components is calculated, followed by the dissolution rate of the eutectic mixture. Based on the thermodynamic parameters (entropy), the eutectic should have a more rapid dissolution rate than the other mixtures. By these analyses, it is also possible to obtain information on the performance of a tablet in terms of bioavailability. This approach also can evaluate the higher bioavailability of a eutectic versus mixtures of the individual components.

Scanning Electron Microscopy (SEM) can be used by performing a scanning EM of each pure component, on the eutectic, and on the mixtures, and observing the different crystal morphology by pointing out the differently shaped particles.

Methods of Administering Eutectic Compositions

Appropriate methods of administering a pharmaceutical composition of the invention to a subject will depend, for example, on the age of the subject, whether the subject is active or inactive at the time of administering, whether the subject is experiencing symptoms of a disease or condition at the time of administering, the extent of the symptoms, and the chemical and biological properties of the API (e.g. solubility, digestibility, bioavailability, stability and toxicity). In some embodiments, the pharmaceutical composition is administered for oral or transmucosal absorption.

Methods of administering compositions for oral absorption are well known in the art. For example, a composition may be administered orally through tablets, capsules, pills, or powders. In these embodiments, the compositions are absorbed by the gastrointestinal tract after swallowing. In certain embodiments, the composition lacks a film or membrane (e.g., a semipermeable membrane).

Methods of administering compositions for transmucosal absorption are well known in the art. For example, a composition may be administered for buccal absorption through buccal tablets, lozenges, buccal powders, and buccal spray solutions. A composition may be administered for sublingual absorption through sublingual tablets, sublingual films, liquids, sublingual powders, and sublingual spray solutions. In certain embodiments, the composition lacks a film or membrane (e.g., a semipermeable membrane). A composition may be administered for intranasal absorption through nasal sprays. A composition may be administered for pulmonary absorption through aerosolized compositions and inhalable dried powders. Because mannitol powder is an inhalation product in the U.S. (trade name: Aridol®; Pharmaxis Ltd.), inhalation may be an especially beneficial form of administration. When administered via sprays or aerosolized compositions, a composition may be prepared with saline as a solution, employ benzyl alcohol or other suitable preservatives, or include absorption promoters to enhance bioavailability, fluorocarbons, and/or other solubilizing or dispersing agents.

Doses and dosing regimens can be determined by one of skill in the art according to the needs of a subject to be treated. The skilled worker may take into consideration factors such as the age or weight of the subject, the severity of the disease or condition being treated, and the response of the subject to treatment. A composition of the invention can be administered, for example, as needed or on a daily basis.

In some embodiments, a composition can be administered immediately prior to sleep or several hours before sleep. Administration prior to sleep may be beneficial by providing the therapeutic effect before the onset of the symptoms of the disease or condition being treated. Dosing may take place over varying time periods. For example, a dosing regimen may last for 1 week, 2 weeks, 3 weeks, 4 weeks, 5 weeks, 6 weeks, 7 weeks, 8 weeks, 9 weeks, 10 weeks, 11 weeks, 12 weeks, or longer. In some embodiments, a dosing regimen will last 1 month, 2 months, 3 months, 4 months, 5 months, 6 months, 7 months, 8 months, 9 months, 10 months, 11 months, 12 months, or longer.

Therapeutic Uses

The pharmaceutical compositions of the invention may be employed for treating or preventing the development of fibromyalgia syndrome, also known as fibrositis (see, e.g., Moldofsky et al. J Rheumatol 38(12):2653-2663 (2011) and Thomas, J Rheumatol 38(12):2499-2500 (2011)). Fibromyalgia is a chronic, non-inflammatory rheumatic disorder. The American College of Rheumatology (ACR) published classification criteria for fibromyalgia in 1990 (Wolfe, F., et al., Arthritis and Rheumatism 33:160-172 (1990)). Subsequently, a modification to the ACR criteria been published (Wolfe et al., J Rheumatol 38(6):1113-22 (2011)). Diagnostic criteria have also been published by an international network of working groups called, "Outcome Measures in Rheumatology" clinical trials or OMERACT (Mease P, et al. J Rheumatol. 2009; 36(10):2318-29.). Fibromyalgia is traditionally characterized by stiffness or diffuse pain, aches, muscle soreness, sleep disturbances or fatigue. The pain is generally widespread and sometimes localized at specific "tender points," which may bring on widespread pain and muscle spasm when touched. Other symptoms include mental and emotional disturbances such as poor concentration and irritability, neuropsychiatric symptoms such as depression and anxiety, joint swelling, headache, numbness. Fibromyalgia is associated with nonrefreshing sleep, tiredness, sleepiness, reflux, mental fog and cognitive impairments including difficulty multi-tasking. Fibromyalgia also is often comorbid with sleep disorders, fatigue, non-restorative sleep, anxiety, and depression. The compositions and methods of the invention can be used to treat any one of the above-identified conditions, and any combination thereof.

Some practitioners further classify fibromyalgia into two categories—primary or secondary-concomitant fibromyalgia. Generally, primary fibromyalgia syndrome can be considered fibromyalgia occurring in the absence of another significant condition whereas secondary-concomitant fibromyalgia can be considered fibromyalgia occurring in the presence of another significant medical disorder, which may have been caused by or is merely associated with the patient's fibromyalgia. Secondary or concomitant fibromyalgia can include fibromyalgia in patients with classical or definite rheumatoid arthritis, osteoarthritis of the knee or hand, low back pain syndromes, cervical pain syndromes, cancer pain syndromes, temporomandibular joint disorders, migraine headaches, menopause, post-traumatic stress disorder and interstitial cystitis or painful bladder syndrome (or combinations thereof).

The compositions of the invention also may be employed for treating or preventing the development (either the initiation, consolidation or perpetuation) of a PTSD symptom following a traumatic event. A traumatic event is defined as a direct personal experience that involves actual or threatened death or serious injury, or other threat to one's physical integrity, or witnessing an event that involves death, injury, or a threat to the physical integrity of another person; or learning about unexpected or violent death, serious harm, or threat of death or injury experienced by a family member or other close associate. Traumatic events that are experienced directly include, but are not limited to, military combat, violent personal assault (sexual assault, physical attack, robbery, mugging), being kidnapped, being taken hostage, terrorist attack, torture, incarceration as a prisoner of war or in a concentration camp, natural or manmade disasters, severe automobile accidents, or being diagnosed with a life-threatening illness. For children, sexually traumatic events may include developmentally inappropriate sexual experiences without threatened or actual violence or injury. Witnessed events include, but are not limited to, observing the serious injury or unnatural death of another person due to violent assault, accident, war, or disaster or unexpectedly witnessing a dead body or body parts. Events experienced by others that are learned about may include, but are not limited to, violent personal assault, serious accident, or serious injury experienced by a family member or a close friend, learning about the sudden, unexpected death of a family member or a close friend, or learning that one's child has a life-threatening disease. The disorder may be especially severe or long lasting when the stressor is of human design (e.g., torture or rape). The initiation of a PTSD symptom typically occurs immediately following the traumatic event, during which the symptoms of PTSD appear and become increasingly severe. One theory of how PTSD develops is that there is a type of "learning" or reinforcement process during which the memories of the trauma are engrained in the mind. As these memories become more fixed (a process called consolidation), symptoms such as flashbacks and nightmares grow in severity and frequency. Interventions during this critical time may prevent some patients from developing full-blown PTSD. The consolidation of a PTSD symptom typically occurs during the weeks and months following a traumatic event. A person's memories of that event become consolidated into highly vivid and concrete memories that are re-experienced with increasing frequency either as flashbacks or nightmares. During this time, hyperarousal symptoms and avoidant behavior can become increasingly severe and disabling. The perpetuation of a PTSD symptom occurs once traumatic memories are consolidated, and the re-experienced symptoms (flashbacks and nightmares) and hyperarousal symptoms become persistent and remain at a level that is functionally disabling to the patient.

The compositions of the invention may be used to treat different phases of PTSD development at various time intervals after a traumatic event. For example, treating the initiation phase of PTSD may require the administration of a composition of the invention soon after the traumatic event, for example within the first week, within the second week, within the third week, or within the fourth week or later. By contrast, when treating the consolidation phase of PTSD, the skilled worker may be able to administer a composition of the invention later after the traumatic event and later during the development of the symptoms, for example, within the first month, within the second month, or within the third month or later. The perpetuation phase of PTSD may be treated with a composition of the invention administered 3 months or longer after the traumatic event, for example within the third month, within the fourth month, within the fifth month, or later. As a result of treatment at the initiation, consolidation, or perpetuation phase, PTSD symptoms will be ameliorated or be eliminated.

The compositions of the invention also can be used to treat traumatic brain injury (TBI). TBI is associated with sleep disorders, sleep disturbances, fatigue, non-restorative sleep, anxiety, and depression. The compositions and methods of the invention also can be used to treat any of the above conditions, in combination with or independently of treating TBI.

The compositions of the invention also can be used to chronic traumatic encephalopathy (CTE). CTE is associated with sleep disorders, sleep disturbances, fatigue, non-restorative sleep, anxiety, and depression. The compositions and methods of the invention also can be used to treat any of the above conditions, in combination with or independently of treating CTE.

The compositions and methods of the invention may be used to treat sleep disorders or sleep disturbances. A "sleep disorder" may be any one of four major categories of sleep dysfunction (DSM-IV, pp. 551-607; see also The International Classification of Sleep Disorders: (ICSD) Diagnostic and Coding Manual, 1990, American Sleep Disorders Association). One category, primary sleep disorders, comprises sleep disorders that do not result from another mental disorder, a substance, or a general medical condition. They include without limitation primary insomnia, primary hypersomnia, narcolepsy, circadian rhythm sleep disorder, nightmare disorder, sleep terror disorder, sleepwalking disorder, REM sleep behavior disorder, sleep paralysis, day/night reversal and other related disorders; substance-induced sleep disorders; and sleep disorders due to a general medical condition. Primary insomnia non-restorative sleep is described by the DSM-IV-TR as a type of primary insomnia wherein the predominant problem is waking up feeling unrefreshed or nonrefreshed. A second category comprises those sleep disorders attributable to substances, including medications and drugs of abuse. A third category comprises sleep disturbances arising from the effects of a general medical condition on the sleep/wake system. A fourth category of sleep disorders comprises those resulting from an identifiable mental disorder such as a mood or anxiety disorder. A fifth category of sleep disorders comprises those described as non-restorative sleep. One definition of non-restorative sleep is in the DSM-IV-TR as a type of primary insomnia (A1.3) wherein the predominant problem is waking up feeling unrefreshed or nonrefreshed. Symptoms of each category of sleep disorder are known in the art. A "sleep disturbance" may be an impairment in refreshing sleep. Such a clinical diagnosis may be made based on a patient's self described feeling of fatigue upon waking or the patient's report of poor quality sleep. Such impediments to good quality sleep may be described as shallow sleep or frequent awakenings which may be associated with an increase in the Cyclic Alternating Pattern (CAP) A2 or A3 rate or cycle duration or an increase in the normalized CAP A2+A3 which is determined by CAP (A2+A3)/CAP (A1+A2+A3) in non-REM sleep (see, e.g., Moldofsky et al, J Rheumatol 38(12): 2653-2663 (2011) and Thomas, J Rheumatol 38(12):2499-2500 (2011)), alpha rhythm contamination in non-REM sleep, or absence of delta waves during deeper physically restorative sleep. Such "sleep disturbances" may or may not rise to the level of a "sleep disorder" as defined in the DSM-IV, although they may share one or more symptom in common. Symptoms of sleep disturbances are known in the art. Among the known symptoms are groggy or spacey feelings, tiredness, feelings of being run down, and having difficulty concentrating during waking hours. Among the sleep-related conditions that may be treated with the methods and compositions of the invention are dyssomnias (e.g., intrinsic sleep disorders such as sleep state misperception, psychophysiological insomnia, idiopathic insomnia, obstructive sleep apnea syndrome, central sleep apnea syndrome, central alveolar hypoventilation syndrome, restless leg syndrome, and periodic limb movement disorder; extrinsic sleep disorders such as environmental sleep disorder, adjustment sleep disorder, limit-setting sleep disorder, stimulant-dependent sleep disorder, alcohol-dependent sleep disorder, toxin-induced sleep disorder, sleep onset association disorder, hypnotic dependent sleep disorder, inadequate sleep hygiene, altitude insomnia, insufficient sleep syndrome, nocturnal eating syndrome, and nocturnal drinking syndrome; and circadian rhythm sleep disorders such as jet lag syndrome, delayed sleep phase syndrome, advanced sleep phase syndrome, shift work sleep disorder, non-24 hour sleep-wake disorder, and irregular sleep-wake patterns), parasomnias (e.g., arousal disorders such as sleepwalking, confusional arousals, and sleep terrors and sleep-wake transition disorders such as rhythmic movement disorder, sleep talking and sleep starts, and nocturnal leg cramps), and sleep disorders associated with medical or psychiatric conditions or disorders. The compositions of the invention also can be used to treat muscle spasms. Muscle spasms can be associated with muscle pain, e.g., back pain. The compositions and methods of the invention also can be used to treat any of the above conditions, in combination with or independently of treating muscle spasms.

Basing Agents

The compositions of the invention may include a basifying agent. As used herein, a "basifying agent" refers to an agent (e.g., a substance that increases the local pH of a liquid comprising Cyclobenzaprine HCl, including potassium dihydrogen phosphate (monopotassium phosphate, monobasic potassium phosphate, $KH_2PO_4$), dipotassium hydrogen phosphate (dipotassium phosphate, dibasic potassium phosphate, $K_2HPO_4$), tripotassium phosphate ($K_3PO_4$), sodium dihydrogen phosphate (monosodium phosphate, monobasic sodium phosphate, $NaH_2PO_4$), disodium hydrogen phosphate (disodium phosphate, dibasic sodium phosphate, $Na_2HPO_4$), trisodium phosphate ($Na_3PO_4$), trisodium citrate anhydrous, bicarbonate or carbonate salts, borate, hydroxide, silicate, nitrate, dissolved ammonia, the conjugate bases of some organic acids (including bicarbonate), and sulfide) that raises the pH of a solution containing Cyclobenzaprine HCl. Without wishing to be bound by theory, a basifying agent, while providing beneficial pharmacokinetic attributes to pharmaceutical compositions comprising Cyclobenzaprine HCl, also may destabilize the Cyclobenzaprine HCl due to interactions between the HCl and basifying agent. Thus, a eutectic composition as described herein may be especially useful in compositions comprising a basifying agent.

Excipients

In some embodiments, a composition of the invention is useful as a medicament. In some embodiments, the invention provides for the use of a composition of the invention in the manufacture of a medicament. In some embodiments, it may be beneficial to include one or more excipients in the compositions of the invention. One of skill in the art would appreciate that the choice of any one excipient may influence the choice of any other excipient. For example, the choice of a particular excipient may preclude the use of one or more additional excipient because the combination of excipients would produce undesirable effects. One of skill in the art would be able to empirically determine which additional excipients, if any, to include in the formulations of the invention. For example, Cyclobenzaprine HCl can be combined with at least one pharmaceutically acceptable carrier such as a solvent, bulking agents, binder, humectant, disintegrating agent, solution retarder, disintegrant, glidant, absorption accelerator, wetting agent, solubilizing agent, lubricant, sweetening agent, or flavorant agent. A "pharmaceutically acceptable carrier" refers to any diluent or excipient that is compatible with the other ingredients of the formulation, and which is not deleterious to the recipient. A pharmaceutically acceptable carrier can be selected on the basis of the desired route of administration, in accordance with standard pharmaceutical practices.

Bulking Agents

In some embodiments, it may be beneficial to include a bulking agent in the compositions of the invention. Bulking agents are commonly used in pharmaceutical compositions to provide added volume to the composition. Bulking agents are well known in the art. Accordingly, the bulking agents described herein are not intended to constitute an exhaustive list, but are provided merely as exemplary bulking agents that may be used in the compositions and methods of the invention.

Exemplary bulking agents may include carbohydrates, sugar alcohols, amino acids, and sugar acids. Bulking agents include, but are not limited to, mono-, di-, or poly-, carbohydrates, starches, aldoses, ketoses, amino sugars, glyceraldehyde, arabinose, lyxose, pentose, ribose, xylose, galactose, glucose, hexose, idose, mannose, talose, heptose, glucose, fructose, methyl a-D-glucopyranoside, maltose, lactone, sorbose, erythrose, threose, arabinose, allose, altrose, gulose, idose, talose, erythrulose, ribulose, xylulose, psicose, tagatose, glucosamine, galactosamine, arabinans, fructans, fucans, galactans, galacturonans, glucans, mannans, xylans, inulin, levan, fucoidan, carrageenan, galactocarolose, pectins, amylose, pullulan, glycogen, amylopectin, cellulose, microcrystalline cellulose, pustulan, chitin, agarose, keratin, chondroitin, dermatan, hyaluronic acid, xanthin gum, sucrose, trehalose, dextran, lactose, alditols, inositols, sorbitol, mannitol, glycine, aldonic acids, uronic acids, aldaric acids, gluconic acid, isoascorbic acid, ascorbic acid, glucaric acid, glucuronic acid, gluconic acid, glucaric acid, galacturonic acid, mannuronic acid, neuraminic acid, pectic acids, maize starch, and alginic acid.

Disintegrants

In some embodiments, it may be beneficial to include a disintegrant in the compositions of the invention. Disintegrants aid in the breakup of solid compositions, facilitating delivery of an active pharmaceutical composition. Disintegrants are well known in the art. Some disintegrants have been referred to as superdisintegrants because they have fast properties, and may be used as disintegrants in the context of the invention. Accordingly, the disintegrants described herein are not intended to constitute an exhaustive list, but are provided merely as exemplary disintegrants that may be used in the compositions and methods of the invention. Exemplary disintegrants include crospovidone, microcrystalline cellulose, sodium carboxymethyl cellulose, methyl cellulose, sodium starch glycolate, calcium carboxymethyl croscarmellose sodium, polyvinylpyrrolidone, lower alkyl-substituted hydroxypropyl cellulose, Indion 414, starch, pre-gelatinized starch, calcium carbonate, gums, sodium alginate, and Pearlitol Flash®. Pearlitol Flash® (Roquette) is a mannitol-maize starch disintegrant that is specifically designed for orally dispersible tablets (ODT). Certain disintegrants have an effervescent quality.

Glidants

In some embodiments, it may be beneficial to include a glidant in the compositions of the invention. Glidants aid in the ability of a powder to flow freely. Glidants are well known in the art. Accordingly, the glidants described herein are not intended to constitute an exhaustive list, but are provided merely as exemplary glidants that may be used in the compositions and methods of the invention. Exemplary glidants include colloidal silica (silicon dioxide), magnesium stearate, starch, talc, glycerol behenate, DL-leucine, sodium lauryl sulfate, calcium stearate, and sodium stearate.

Lubricants

In some embodiments, it may be beneficial to include a lubricant in the compositions of the invention. Lubricants help keep the components of a composition from clumping. Lubricants are well known in the art. Accordingly, the lubricants described herein are not intended to constitute an exhaustive list, but are provided merely as exemplary lubricants that may be used in the compositions and methods of the invention. Exemplary lubricants include calcium stearate, magnesium stearate, stearic acid, sodium stearyl fumarate, vegetable based fatty acids, talc, mineral oil, light mineral oil, hydrogenated vegetable oil (e.g., peanut oil, cottonseed oil, sunflower oil, sesame oil, olive oil, corn oil, safflower oil, canola oil, coconut oil and soybean oil), silica, zinc stearate, ethyl oleate, ethyl laurate.

Sweeteners

In some embodiments, it may be beneficial to include a sweetener in the compositions of the invention. Sweeteners help improve the palatability of the composition by conferring a sweet taste to the composition. Sweeteners are well known in the art. Accordingly, the sweeteners described herein are not intended to constitute an exhaustive list, but are provided merely as exemplary sweeteners that may be used in the compositions and methods of the invention. Exemplary sweeteners include, without limitation, compounds selected from the saccharide family such as the mono-, di-, tri-, poly-, and oligosaccharides; sugars such as sucrose, glucose (corn syrup), dextrose, invert sugar, fructose, maltodextrin and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexaresorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide many also be used.

Flavorants

In some embodiments, it may be beneficial to include a flavorant in the compositions of the invention. Flavorants help improve the palatability of the composition by conferring a more desirable taste to the composition. Flavorants are well known in the art. Accordingly, the flavorants described herein are not intended to constitute an exhaustive list, but are provided merely as exemplary flavorants that may be used in the compositions and methods of the invention. Exemplary flavorants include, without limitation, natural and/or synthetic (i.e., artificial) compounds such as mint, peppermint, spearmint, wintergreen, menthol, anise, cherry, strawberry, watermelon, grape, banana, peach, pineapple, apricot, pear, raspberry, lemon, grapefruit, orange, plum, apple, lime, fruit punch, passion fruit, pomegranate, chocolate (e.g., white, milk, dark), vanilla, caramel, coffee, hazelnut, cinnamon, combinations thereof, and the like.

Coloring Agents

Coloring agents can be used to color code the composition, for example, to indicate the type and dosage of the therapeutic agent therein. Coloring Agents are well known in the art. Accordingly, the coloring agents described herein are not intended to constitute an exhaustive list, but are provided merely as exemplary coloring agents that may be used in the compositions and methods of the invention. Exemplary coloring agents include, without limitation, natural and/or artificial compounds such as FD & C coloring agents, natural juice concentrates, pigments such as titanium oxide, silicon dioxide, and zinc oxide, combinations thereof, and the like.

Combination Therapy

As described above, the compositions and methods of the invention may be used to treat PTSD, depression, fibromyalgia, traumatic brain injury, sleep disorder, non-restorative sleep, chronic pain, and anxiety disorder. Any of the methods of treatment described also may be combined with a psychotherapeutic intervention to improve the outcome of the treatment. Exemplary psychotherapeutic interventions directed at either modifying traumatic memories or reducing emotional responses to traumatic memories, including psychological debriefing, cognitive behavior therapy and eye movement desensitization and reprocessing, systematic desensitization, relaxation training, biofeedback, cognitive processing therapy, stress inoculation training, assertiveness training, exposure therapy, combined stress inoculation training and exposure therapy, combined exposure therapy, and relaxation training and cognitive therapy. In each case, the goal of the intervention involves either modifying traumatic memories or reducing emotional responses to traumatic memories. The intended result is generally an improvement in the symptoms of PTSD or the reduction of occurrences of symptoms, as evidenced in terms of physiological responding, anxiety, depression, and feelings of alienation.

In some embodiments of the invention, a composition is combined with a drug which may further alleviate the symptoms of PTSD, depression, fibromyalgia, traumatic brain injury, sleep disorder, non-restorative sleep, chronic pain, or anxiety disorder. The drugs include an alpha-1-adrenergic receptor antagonist, a beta-adrenergic antagonist, an anticonvulsant, a selective serotonin reuptake inhibitor, a serotonin-norepinephrine reuptake inhibitor, and an analgesic. Exemplary anticonvulsants include carbamazepine, gabapentin, lamotrigine, oxcarbazepine, pregabalin, tiagabine, topiramate, and valproate. An exemplary alpha-1-adrenergic receptor antagonist is prazosin. Exemplary selective serotonin reuptake inhibitors or serotonin-norepinephrine reuptake inhibitors include, bupropion, citalopram, desvenlafaxine, duloxetine, escitalopram, fluoxetine, escitalopram, fluvoxamine, milnacipran, paroxetine, sertraline, trazodone, and venlafaxine. Exemplary analgesics include pregabalin, gabapentin, acetaminophen, tramadol, and non-steroidal anti-inflammatory drugs (e.g., ibuprofen and naproxen sodium). Additional drugs that can be used in combination with the compositions of the invention include sodium oxybate, zolpidem, pramipexole, modafinil, temazepam, zaleplon, and armodafinil.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

The following examples are set forth as being representative of the present invention. These examples are not to be construed as limiting the scope of the invention as these and other equivalent embodiments will be apparent in view of the present disclosure, figures, and accompanying claims.

EXAMPLES

Example 1: Wet Granulation

To produce a δ mannitol eutectic with cyclobenzaprine HCl, the following protocol was used:
1. Load 52.830% cyclobenzaprine HCl (w/w) (e.g., 368.4 g) and 47.170% mannitol (w/w) (e.g., 328.9 g) into a high shear granulator.
2. Optionally, mix the cyclobenzaprine HCl and mannitol for 5 minutes using an impeller speed of 500 rpm.
3. Mix for 1 minute under the following conditions: impeller speed, 200 rpm; chopper speed, 2000 rpm; time, 2 min.
4. While continuing to mix, spray water (10% w/w) onto powder blend.
5. Mix for 1 additional minute.
6. Dry in fluid bed dryer to a loss on drying (LOD) of not more than (NMT) 2.0% under the following conditions: air flow, 100 m$^3$/h; wet temperature: 65° C.; LOD: 0.31%.
7. Collect the sample.

As one example, a cyclobenzaprine HCl-mannitol δ eutectic can be prepared by wet granulation by mixing 368.4 g of cyclobenzaprine HCl, 328.9 g Pearlitol 100SD, and 55.8 g water. Using those amounts produced a net yield of 662.2 g of dried granules, for a total of 95% recovery.

A eutectic mixture formed by the above method was then blended with other excipients as follows:
Cyclobenzaprine eutectic mixture: 232.4 g
Dye D&C Yellow #10 Lake: 0.667 g
Pearlitol Flash: 1144 g
Crospovidone-Kollidon CL: 87.7 g
Dibasic potassium phosphate, anhydrous: 52.7 g
Spearmint flavor, natural and artificial: 83.3 g
Colloidal silicon dioxide: 22.0 g
Sodium stearyl fumarate (PRUV): 43.8
For tableting, exemplary compression parameters include compression at 30 rpm with a compression force of 5.0 kN, optionally with pre-compression (3.0 kN) to form a tablet with a weight variation of less than 2%, a disintegration time of approximately 40-50 seconds, and a hardness of approximately 3 kp. Alternative exemplary compression parameters include compression at 40 rpm (5.5 kN compression force, 3.0 kN pre-compression force), resulting in a tablet weight variation of less than 2%, a disintegration time of approximately 90 seconds and a hardness of 3.0-3.5 kp.

Example 2: Fluid Bed Drying

To create a tablet comprising cyclobenzaprine using fluid bed drying, the following protocol was used:
β mannitol with a particle size below 20 microns was deposited in the basin at the bottom of the fluid bed dryer. A warm flow of air was then initiated to induce vigorous turbulence inside the chamber. After all the matter in the chamber was under controlled and constant turbulence, a water solution with cyclobenzaprine was linked to the nozzle present in the center of the equipment. This liquid was spread by a peristaltic pump on the mannitol particles in turbulence from the bottom to the filter and small, almost nebulized drops were wet the surface of the mannitol particles. This liquid phase present on the surface of the mannitol induced partial solubilization of the mannitol particle surfaces. Through the process of the hot air removing the moisture, the eutectic formed on the surface of the particles, beginning in the metastable phase and subsequently crystallizing. Preliminary analyses carried out by Thermal Analysis (Differential Scanning calorimetry) and X-ray Powder Diffraction (XRPD) on the granules confirm the presence of the eutectic components inside the mixture and homogeneous distribution of the cyclobenzaprine HCl in the entire matrix. Without wishing to be bound by theory, this interaction of the cyclobenzaprine with mannitol induced by spraying to form the eutectic may promote more chemical stability of the drug substance than a simple mechanical mixture. Interestingly, the process produced granules with a β mannitol core and a δ mannitol-cyclobenzaprine eutectic outer surface. These granules had improved tableting properties over eutectics formed by other methods.

What is claimed is:

1. A pharmaceutical composition comprising a eutectic of δ-mannitol and Cyclobenzaprine HCl, wherein the eutectic comprises 65%±2% Cyclobenzaprine HCl and 35%±2% δ-mannitol by weight.
2. The pharmaceutical composition of claim 1, wherein the Cyclobenzaprine HCl is micronized Cyclobenzaprine HCl.
3. The pharmaceutical composition of claim 1, further comprising a basifying agent.
4. The pharmaceutical composition of claim 3, wherein the basifying agent is $K_2HPO_4$, $Na_2HPO_4$, or anhydrous trisodium citrate.
5. The pharmaceutical composition of claim 1, wherein said composition comprises granules.
6. The pharmaceutical composition of claim 5, wherein said granules comprise Cyclobenzaprine HCl and δ mannitol.
7. A method of manufacturing the pharmaceutical composition of claim 1, comprising mixing Cyclobenzaprine HCl and mannitol in the presence of a solvent.
8. The method of claim 7, wherein the mannitol is β mannitol or δ mannitol.
9. The method of claim 7, wherein said mixing is wet granulation mixing.
10. The method of claim 7, wherein the solvent is water, an alcohol or a mixture thereof.
11. The method of claim 10, wherein said alcohol is methanol or ethanol.
12. The method of claim 9, further comprising drying the mixture after said wet granulation.
13. The method of claim 12, wherein said wet granulation and drying are repeated one or more times.
14. The method of claim 9, further comprising crystallizing the Cyclobenzaprine HCl-mannitol mixture after said wet granulation.
15. The method of claim 14, wherein said wet granulation and crystallization are repeated one or more times.
16. A method of manufacturing the pharmaceutical composition of claim 1 comprising fluid bed drying a mixture of Cyclobenzaprine HCl, mannitol, and a solvent.
17. The method of claim 16, wherein the mannitol is β mannitol or δ mannitol.
18. The method of claim 16, wherein the solvent is water, an alcohol or a mixture thereof.
19. The method of claim 18, wherein the alcohol is methanol or ethanol.
20. The method of claim 16, wherein the Cyclobenzaprine HCl is dissolved in the solvent and sprayed onto β mannitol particles inside a fluid bed dryer.
21. The pharmaceutical composition of claim 1, wherein the δ-mannitol eutectic melts at 134° C.±3° C.
22. The method of claim 7, wherein Cyclobenzaprine HCl is mixed with β mannitol.
23. The method of claim 22, wherein the β mannitol converts to δ mannitol.

* * * * *